US007402309B2

(12) United States Patent
Fischetti et al.

(10) Patent No.: US 7,402,309 B2
(45) Date of Patent: Jul. 22, 2008

(54) **PHAGE-ASSOCIATED LYTIC ENZYMES FOR TREATMENT OF *BACILLUS ANTHRACIS* AND RELATED CONDITIONS**

(75) Inventors: Vincent A. Fischetti, West Hempstead, NY (US); Raymond Schuch, New York, NY (US); Daniel Nelson, New York, NY (US)

(73) Assignee: The Rockefeller University, New York, NY (US)

( * ) Notice: Subject to any disclaimer, the term of this patent is extended or adjusted under 35 U.S.C. 154(b) by 495 days.

(21) Appl. No.: 10/849,948

(22) Filed: May 19, 2004

(65) Prior Publication Data

US 2005/0004030 A1 Jan. 6, 2005

Related U.S. Application Data

(63) Continuation-in-part of application No. PCT/US03/15719, filed on May 19, 2003.

(60) Provisional application No. 60/380,875, filed on May 17, 2002.

(51) Int. Cl.
| | |
|---|---|
| A61K 38/46 | (2006.01) |
| C12Q 1/34 | (2006.01) |
| C12P 21/06 | (2006.01) |
| C12N 15/00 | (2006.01) |
| C12N 9/48 | (2006.01) |
| C12N 5/10 | (2006.01) |
| C12N 1/21 | (2006.01) |
| C07H 21/00 | (2006.01) |
| C07K 14/00 | (2006.01) |

(52) U.S. Cl. .................. 424/94.6; 424/94.67; 435/212; 435/18; 435/69.1; 435/320.1; 435/325; 435/252.3; 536/23.2; 530/350

(58) Field of Classification Search .............. 435/212, 435/18, 69.1, 320.1, 325, 252.3; 536/23.2; 530/350; 424/94.6, 94.67

See application file for complete search history.

(56) References Cited

U.S. PATENT DOCUMENTS

2002/0127215 A1    9/2002   Loomis et al.

FOREIGN PATENT DOCUMENTS

WO    WO 03/010316 A1    2/2003

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Brown, Eric R. et al.; "Specific Identification of *Bacillus Anthracis* by Means of a Variant Bacteriophage"; United States Department of Health, Education and Welfare, Communicable Disease Center, Public Health Service, Chamblee, Georgia, pp. 34-39., 1954.
Nelson, Daniel et al.; "Prevention and elimination of upper respiratory colonization of mice by group A streptococci by using a bacteriophage lytic enzyme"; Proc. Natl. Acad. Sci., 2001, vol. 98, No. 7, pp. 4107-4112.
Schuch, Raymond et al.; "A bacteriolytic agent that detects and kills *Bacillus anthracis*;" Nature, vol. 418; Aug. 22, 2002; pp. 884-889.
Internet excerpt entitled "Bacteriophage;" New Horizons Diagnostics Inc.; obtained at the internet address: nhdiag.com/phage.shtml; Nov. 5, 2003; two pages.
Internet excerpt entitled "Bacteriophage;" New Horizons Diagnostics Inc.; obtained at the internet address: nhdiag.com/phage.shtml; Jan. 13, 2004; two pages.
Internet excerpt entitled "*Bacillus anthracis* (spore) Lateral Flow Screening Assay;" New Horizons Diagnostics Inc.; obtained at the internet address: nhdiag.com/anthrax.shtml; Jan. 13, 2004; two pages.

* cited by examiner

*Primary Examiner*—Delia M Ramirez
(74) *Attorney, Agent, or Firm*—Brinks Hofer Gilson & Lione

(57) ABSTRACT

The present disclosure relates to methods, compositions and articles of manufacture useful for the treatment of *Bacillus anthracis* and *B. cereus* bacteria and spores, and related conditions. The disclosure further relates to methods and compositions for the identification of a phage associated lytic enzyme to rapidly and specifically detect and kill *Bacillus anthracis* and other bacteria. Related articles of manufacture, methods of degrading spores and methods of treatment of infections or bacteria populations of, or subjects exposed to or at risk for exposure to, *Bacillus anthracis* are also provided.

20 Claims, 6 Drawing Sheets

Gamma lysin ORF and protein

```
  1  atggaaatccaaaaaaaattagttgatccaagtaagtatggtaca
     M  E  I  Q  K  K  L  V  D  P  S  K  Y  G  T
 46  aagtgtccgtatacaatgaagcctaaatatatcactgttcacaac
     K  C  P  Y  T  M  K  P  K  Y  I  T  V  H  N
 91  acatataatgatgctccagctgaaaatgaagtgagttacatgatt
     T  Y  N  D  A  P  A  E  N  E  V  S  Y  M  I
136  agtaacaataatgaggtgtcgtttcatattgcagtagatgacaag
     S  N  N  N  E  V  S  F  H  I  A  V  D  D  K
181  aaagcgattcaaggtattccgttggaacgtaatgcatgggcttgc
     K  A  I  Q  G  I  P  L  E  R  N  A  W  A  C
226  ggagacggcaatggttcggggaatcgtcaatccatttctgtagaa
     G  D  G  N  G  S  G  N  R  Q  S  I  S  V  E
271  atctgttattcaaaatcaggaggagatagatactataaagctgag
     I  C  Y  S  K  S  G  G  D  R  Y  Y  K  A  E
316  gataatgctgttgatgttgtacgacaacttatgtctatgtacaat
     D  N  A  V  D  V  V  R  Q  L  M  S  M  Y  N
361  attccgattgaaaatgttcgaactcatcaatcctggtcaggtaaa
     I  P  I  E  N  V  R  T  H  Q  S  W  S  G  K
406  tattgtccgcatagaatgttagctgagggaaggtggggagcattc
     Y  C  P  H  R  M  L  A  E  G  R  W  G  A  F
451  attcagaaggttaagaatgggaatgtggcgactacttcaccaaca
     I  Q  K  V  K  N  G  N  V  A  T  T  S  P  T
496  aaacaaaacatcatccaatcaggggctttctaccgtatgaaacc
     K  Q  N  I  I  Q  S  G  A  F  S  P  Y  E  T
541  cctgatgttatgggagcattaacgtcacttaaaatgacagctgat
     P  D  V  M  G  A  L  T  S  L  K  M  T  A  D
586  tttatcttacaatcggatggattaacttatttatttccaaaccg
     F  I  L  Q  S  D  G  L  T  Y  F  I  S  K  P
631  acttcagatgcacaactaaaagcaatgaaagaataccttgaccgt
     T  S  D  A  Q  L  K  A  M  K  E  Y  L  D  R
675  aaaggttggtggtatgaagttaaataa 702
     K  G  W  W  Y  E  V  K  *
```

PHAGE-ASSOCIATED LYTIC ENZYMES FOR TREATMENT OF *BACILLUS ANTHRACIS* AND RELATED CONDITIONS

RELATED APPLICATIONS

This application is a continuation-in-part of patent application number PCT/US03/15719, filed on May 19, 2003, which claims priority to U.S. Provisional Application No. 60/380,875, filed May 17, 2002. The entire contents of the above-identified application is hereby incorporated by reference.

The present disclosure relates to methods, compositions and articles of manufacture useful for the treatment of *Bacillus anthracis* and certain related bacteria, spores thereof, and related conditions. The disclosure further relates to methods and compositions for the identification of a phage associated lytic enzyme to rapidly and specifically detect and kill *Bacillus anthracis* and certain related bacteria.

BACKGROUND

A major problem in medicine has been the development of drug resistant bacteria as more antibiotics are used for a wide variety of illnesses and other conditions. The use of more antibiotics and the number of bacteria showing resistance has prompted longer treatment times. Furthermore, broad, non-specific antibiotics, some of which have detrimental effects on the patient, are now being used more frequently. A related problem with this increased use is that many antibiotics do not penetrate mucus linings easily. Additionally, the number of people allergic to antibiotics appears to be increasing. Accordingly, there is a commercial need for new antibiotics, especially those that operate in new modalities or provide new means to kill pathogenic bacteria.

Attempts have been made to treat bacterial diseases through the use of bacteriophages. However, the direct introduction of bacteriophages into an animal to prevent or fight diseases has certain drawbacks. Specifically, both the bacteria and the phage have to be in the correct and synchronized growth cycles for the phage to attach. Additionally, there must be the right number of phages to attach to the bacteria; if there are too many or too few phages, there will be either no attachment or no production of the lysing enzyme. The phage must also be active enough. The phages are also inhibited by many things including bacterial debris from the organism it is going to attack. Further complicating the direct use of a bacteriophage to treat bacterial infections is the possibility of immunological reactions, rendering the phage non-functional.

Consequently, others have explored the use of safer and more effective means to treat and prevent bacterial infections. In particular, the use of phage associated lytic enzymes has been explored.

Bacteriophage lysins are a class of bacteriolytic agents recently proposed for eradicating the nasopharyngeal carriage of pathogenic streptococci. (Loeffler, J. M., Nelson, D. & Fischetti, V. A. Rapid killing of *Streptococcus pneumoniae* with a bacteriophage cell wall hydrolase. Science 294, 2170-2 (2001); Nelson, D., Loomis, L. & Fischetti, V. A. Prevention and elimination of upper respiratory colonization of mice by group A streptococci by using a bacteriophage lytic enzyme. Proc Natl Acad Sci USA 98, 4107-12 (2001)). Lysins are part of the lytic mechanism used by double stranded DNA (dsDNA) phage to coordinate host lysis with completion of viral assembly. Wang, I. N., Smith, D. L. & Young, R. Holins: the protein clocks of bacteriophage infections. Annu Rev Microbiol 54, 799-825 (2000). Late in infection, lysin translocates into the cell wall matrix where it rapidly hydrolyzes covalent bonds essential for peptidoglycan integrity, causing bacterial lysis and concomitant progeny phage release. Lysin family members exhibit a modular design in which a usually well conserved catalytic domain is fused to a more divergent specificity or binding domain. See, Lopez, R., Garcia, E., Garcia, P. & Garcia, J. L. The pneumococcal cell wall degrading enzymes: a modular design to create new lysins? Microb Drug Resist 3, 199-211 (1997).

SUMMARY

The dormant and durable spore form of *Bacillus anthracis* has been reported to be an ideal biological weapon. (Mock, M. & Fouet, A. Anthrax. Annu Rev Microbiol 55, 647-71 (2001), Inglesby, T. V. et al. Anthrax as a biological weapon, 2002: updated recommendations for management. Jama 287, 2236-52 (2002)). *Bacillus anthracis* spores are extremely virulent in humans and can remain viable in the environment almost indefinitely after release. Once inhaled, spores are transported by alveolar macrophages to mediastinal and peri-bronchial lymph nodes where they germinate; subsequent vegetative clonal expansion causes an overwhelming bacteremia and toxemia. Mortality rates associated with untreated inhalational anthrax can reach 99%, with antibiotic treatment being largely unsuccessful if initiated after the onset of non-specific febrile symptoms. The potential for naturally occurring and genetically engineered antibiotic resistance amplifies the threat of weaponized spores and accentuate needs for improved treatments and methods for spore detection following an intentional release.

An embodiment of the disclosure provides for the extraction and use of a variety of bacterial phage associated holin proteins, chimeric lytic enzymes, and shuffled lytic enzymes, in addition to lytic enzymes, for the treatment of *Bacillus anthracis*. More specifically, the present disclosure provides for a pharmaceutical composition comprising at least one bacteria-associated phage enzyme that is isolated from one or more bacterial species and includes at least one phage lytic enzyme and/or holin protein that may be used for the prophylactic and therapeutic treatment of *Bacillus anthracis*.

Furthermore, the embodiment of the disclosure concerns the extraction and use of a bacterial phage associated lytic enzymes for the treatment and prevention of *Bacillus anthracis*, also referred to simply as anthrax. In one such embodiment, the bacterial phage associated lytic enzyme is prepared by growing gamma phage in an infected bacterium and harvesting the enzyme. In another such embodiment, the bacterial phage associated lytic enzyme is prepared recombinantly by growing a transgenic bacterium that makes the enzyme and then extracting the enzyme from the bacterium.

Experiments were performed that demonstrate the inherent specificity of the enzymes for the rapid detection and killing of *Bacillus anthracis*. The PlyG lysin, isolated and purified from the highly specific gamma phage for *Bacillus anthracis*, quickly and specifically killed *Bacillus anthracis* and members of the anthracis "group" of bacilli.

In one embodiment of the disclosure, the PlyG lysin is sequenced.

In another embodiment, the PlyG lysin is used to prophylactically and therapeutically treat *Bacillus anthracis*.

In yet another embodiment of the disclosure, PlyG lysin is used to detect and identify *Bacillus anthracis*.

In yet another embodiment of the disclosure, shuffled lytic enzymes are used to prophylactically and therapeutically treat bacterial infections caused by *Bacillus anthracis*.

In yet another embodiment of the disclosure, holin proteins are used in conjunction with phage associated lytic enzymes to prophylactically and therapeutically treat bacterial diseases caused by *Bacillus anthracis*. In another embodiment of the disclosure, holin proteins alone are used to prophylactically and therapeutically treat bacterial infections caused by *Bacillus anthracis*. The holin proteins may be shuffled holin proteins or chimeric holin proteins, in either combination with or independent of the lytic enzymes caused by *Bacillus anthracis*.

In yet another embodiment of the disclosure, a chimeric and/or shuffled lytic enzyme is administered parenterally, wherein the phage associated lytic enzyme is administered intramuscularly, intrathecally, subdermally, subcutaneously, or intravenously to treat infections by *Bacillus anthracis* enzyme(s).

It is another object of the disclosure to apply a phage associated shuffled and/or chimeric lytic enzyme intravenously, to treat septicemia and general infections of *Bacillus anthracis*.

In yet another embodiment, chimeric lytic enzymes, shuffled lytic enzymes, "unaltered" versions of the PlyG lysin, holin proteins, and combinations thereof are used to prophylactically and therapeutically treat exposure to *Bacillus anthracis*. In another embodiment, chimeric lytic enzymes, shuffled lytic enzymes, "unaltered" versions of the PlyG lysin, holin proteins, and combinations thereof are used to detect and identify *Bacillus anthracis*. In one embodiment, the phage associated lytic enzyme specific for *Bacillus anthracis* may be used to identify *Bacillus anthracis* in its vegetative state.

While the sequence of PlyG lysin has been isolated from the gamma phage as shown in FIG. 1, other lytic enzymes from bacteriophage specific for *Bacillus anthracis* may be used in place of PlyG. In one embodiment, the DNA encoding the lytic enzyme or holin protein, including their isozymes, analogs, or variants, has been genetically altered. In another embodiment, the lytic enzyme or holin protein, including their isozymes, analogs, or variants, has been chemically altered. In yet another embodiment, the lytic enzyme or holin protein, including their isozymes, analogs, or variants, are used in a combination of natural and modified (genetically or chemically altered) forms. The modified or altered forms of lytic enzymes and holin proteins are made synthetically by chemical synthesis and/or DNA recombinant techniques. The enzymes are made synthetically by chimerization and/or shuffling.

It should be understood that bacteriophage lytic enzyme are enzymes that specifically cleave bonds that are present in the peptidoglycan of bacterial cells. Since the bacterial cell wall peptidoglycan is highly conserved among all bacteria, there are only a few bonds to be cleaved to disrupt the cell wall. Enzymes that cleave these bonds are muramidases, glucosamimidases, endopeptidases, or N-acetyl-muramoyl-L-alanine amidases (hereinafter referred to as amidases). The majority of reported phage enzymes are either muramidases or amidases, and there have been no reports of bacteriophage glucosamidases. Fischetti et al (1974) reported that the C1 streptococcal phage lysin enzyme was an amidase. Garcia et al (1987, 1990) reported that the Cpl lysin from a *S. pneumoniae* from a Cp-1 phage was a lysozyme. Caldentey and Bamford (1992) reported that a lytic enzyme from the phi 6 *Pseudomonas* phage was an endopeptidase, splitting the peptide bridge formed by melodiaminopimilic acid and D-alanine. The *E. coli* T1 and T6 phage lytic enzymes are amidases as is the lytic enzyme from *Listeria* phage (ply) (Loessner et al, 1996). There are also other enzymes which cleave the cell wall.

The present disclosure uses such a lytic enzyme genetically coded for by a particular bacteriophage as either a prophylactic treatment for preventing those who have possibly been exposed to *Bacillus anthracis*, or as a therapeutic treatment for those who have already become ill from the infection. The phage associated lytic enzymes specific for *Bacillus anthracis* and genetically coded by a specific phage can effectively and efficiently break down the cell wall of the *Bacillus anthracis*. It is noted that the semipurified enzyme may lack proteolytic enzymatic activity and therefore may be nondestructive to mammalian proteins and tissues when present during the digestion of the bacterial cell wall.

Another embodiment also provides for chimeric proteins or peptides fragments which include fusion proteins for the aforesaid uses.

A definition of terms used and their applicability to the disclosure are provided as follows:

In this context of the embodiments, the term "lytic enzyme genetically coded for by a bacteriophage" means a polypeptide having at least some lytic activity against the host bacteria. The polypeptide has a sequence that encompasses a native sequence of a lytic enzyme and variants thereof. The polypeptide may be isolated from a variety of sources, such as from phage, or prepared by recombinant or synthetic methods, such as those by Garcia et al. Every polypeptide has two domains. One domain is a choline binding portion at the carboxyl terminal side and the other domain is an amidase activity that acts upon amide bonds in the peptidoglycan at the amino terminal side. Generally speaking, a lytic enzyme according to the disclosure is between 25,000 and 35,000 daltons in molecular weight and comprises a single polypeptide chain; however, this can vary depending on the enzyme chain. The molecular weight most conveniently is determined by assay on denaturing sodium dodecyl sulfate gel electrophoresis and comparison with molecular weight markers.

The term "isolated" means at least partially purified from a starting material. The term "purified" means that the biological material has been measurably increased in concentration by any purification process, including by not limited to, column chromatography, HPLC, precipitation, electrophoresis, etc., thereby partially, substantially or completely removing impurities such as precursors or other chemicals involved in preparing the material. Hence, material that is homogenous or substantially homogenous (e.g., yields a single protein signal in a separation procedure such as electrophoresis or chromatography) is included within the meanings of isolated and purified. Skilled artisans will appreciated that the amount of purification necessary will depend upon the use of the material. For example, compositions intended for administration to humans ordinarily must be highly purified in accordance with regulatory standards.

"A native sequence phage associated lytic enzyme" is a polypeptide having the same amino acid sequence as an enzyme derived from nature. Such native sequence enzyme can be isolated from nature or can be produced by recombinant or synthetic means. The term "native sequence enzyme" specifically encompasses naturally occurring forms (e.g., alternatively spliced or modified forms) and naturally-occurring variants of the enzyme. In one embodiment of the disclosure, the native sequence enzyme is a mature or full-length polypeptide that is genetically coded for by a gene from a bacteriophage specific for *Bacillus anthracis*. Of course, a number of variants are possible and known, as acknowledged in publications such as Lopez et al., Microbial Drug Resistance 3: 199-211 (1997); Garcia et al., Gene 86: 81-88 (1990); Garcia et al., Proc. Natl. Acad. Sci. USA 85: 914-918 (1988); Garcia et al., Proc. Natl. Acad. Sci. USA 85: 914-918 (1988); Garcia et al., Streptococcal Genetics (J. J. Ferretti and Curtis eds., 1987); Lopez et al., FEMS Microbiol. Lett. 100: 439-448 (1992); Romero et al., J. Bacteriol. 172: 5064-5070 (1990); Ronda et al., Eur. J. Biochem. 164: 621-624 (1987) and Sanchez et al., Gene 61: 13-19 (1987). The contents of each of these references, particularly the sequence listings and associated text that compares the sequences, including statements about sequence homologies, are specifically incorporated by reference in their entireties.

"A variant sequence phage associated lytic enzyme" means a functionally active lytic enzyme genetically coded for by a bacteriophage specific for *Bacillus anthracis*, as defined below, having at least 50%, 55%, 60%, 65%, 70%, 75%, 80%, 85%, 90%, 95%, 97%, 98%, 99%, or even at least 99.5% amino acid sequence identity with the sequence shown as SEQ ID No. 1. Of course a skilled artisan readily will recognize portions of this sequence that are associated with functionalities such as binding, and catalyzing a reaction. Accordingly, polypeptide sequences and nucleic acids that encode these sequences are contemplated that comprise at least 75%, 80%, 85%, 90%, 95%, 97%, 98%, 99% or more of each functional domain of SEQ ID No. 1. Such portions of the total sequence are very useful for diagnostics as well as therapeutics/prophylaxis. In fact, sequences as short as 5 amino acids long have utility as epitopic markers for the phage. More desirably, larger fragments or regions of protein having a size of at least 8, 9, 10, 12, 15 or 20 amino acids, and homologous sequences to these, have epitopic features and may be used either as small peptides or as sections of larger proteins according to embodiments. Nucleic acids corresponding to these sequences also are contemplated.

Such phage associated lytic enzyme variants include, for instance, lytic enzyme polypeptides wherein one or more amino acid residues are added, or deleted at the N or C terminus of the sequence of SEQ ID No. 1. In an embodiment one or more amino acids are substituted, deleted, and/or added to any position(s) in the sequence, or sequence portion. Ordinarily, a phage associated lytic enzyme will have at least about (e.g. exactly) 50%, 55%, 60%, 65%, 70%, 75%, amino acid sequence identity with native phage associated lytic enzyme sequences, more preferably at least about (e.g. exactly) 80%, 85%, 90%, 95%, 97%, 98%, 99% or 99.5% amino acid sequence identity. In other embodiments a phage associated lytic enzyme variant will have at least about 50% (e.g. exactly 50%), 55%, 60%, 65%, 70%, 75%, 80%, 85%, 90%, 95%, 97%, 98%, 99%, or even at least 99.5% amino acid sequence identity with the sequence shown as SEQ ID No. 1.

"Percent amino acid sequence identity" with respect to the phage associated lytic enzyme sequences identified herein is defined as the percentage of amino acid residues in a candidate sequence that are identical with the amino acid residues in the phage associated lytic enzyme sequence, after aligning the sequences in the same reading frame and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, such as using publicly available computer software such as blast software. Those skilled in the art can determine appropriate parameters for measuring alignment, including any algorithms needed to achieve maximal alignment over the whole length of the sequences being compared.

In each case, of course conservative amino acid substitutions also may be made simultaneously in determining percent amino acid sequence identity. For example, a 15 amino acid long region of protein may have 50%, 55%, 60%, 65%, 70%, 75%, 80%, 85%, 90%, 95%, 97%, 98%, or 99% sequence homology with a region of SEQ ID No. 1. At the same time, the 15 amino acid long region of the protein may also have up to 0.5%, 1%, 2%, 5%, 10%, 15%, 20%, 30%, 40%, 50%, 65%, 75%, or more amino acids replaced with conservative substitutions. Preferably the region will have fewer than 30%, 20%, 10% or even less conservative substitutions. The "percent amino acid sequence identity" calculation in such cases will be higher than the actual percent sequence identity when conservative amino acid substitutions have been made.

"Percent nucleic acid sequence identity" with respect to the phage associated lytic enzyme sequences identified herein is defined as the percentage of nucleotides in a candidate sequence that are identical with the nucleotides in the phage associated lytic enzyme sequence, after aligning the sequences and introducing gaps, if necessary, to achieve the maximum percent sequence identity. Alignment for purposes of determining percent nucleic acid sequence identity can be achieved in various ways that are within the scope of those skilled in the art, including but not limited to the use of publicly available computer software. Those skilled in the art can determine appropriate parameters for measuring alignment, including any algorithms needed to achieve maximal alignment over the full length of the sequences being compared.

"Polypeptide" refers to a molecule comprised of amino acids which correspond to those encoded by a polynucleotide sequence which is naturally occurring. The polypeptide may include conservative substitutions wherein the naturally occurring amino acid is replaced by one having similar properties, where such conservative substitutions do not alter the function of the polypeptide (see, for example, Lewin "Genes V" Oxford University Press Chapter 1, pp. 9-13 1994).

A "chimeric protein" or "fusion protein" comprises all or (preferably a biologically active) part of a polypeptide of the disclosure operably linked to a heterologous polypeptide. Chimeric proteins or peptides are produced, for example, by combining two or more proteins having two or more active sites. Chimeric protein and peptides can act independently on the same or different molecules, and hence have a potential to treat two or more different bacterial infections at the same time. Chimeric proteins and peptides also are used to treat a bacterial infection by cleaving the cell wall in more than one location.

The term "operably linked" means that the polypeptide of the disclosure and the heterologous polypeptide are fused in-frame. The heterologous polypeptide can be fused to the N-terminus or C-terminus of the polypeptide of the disclosure. Chimeric proteins are produced enzymatically by chemical synthesis, or by recombinant DNA technology. A number of chimeric lytic enzymes have been produced and studied. Gene E-L, a chimeric lysis constructed from bacteriophages phi X174 and MS2 lysis proteins E and L, respectively, was subjected to internal deletions to create a series of new E-L clones with altered lysis or killing properties. The lytic activities of the parental genes E, L, E-L, and the internal truncated forms of E-L were investigated in this study to characterize the different lysis mechanism, based on differences in the architecture of the different membranes spanning domains. Electron microscopy and release of marker enzymes for the cytoplasmic and periplasmic spaces revealed that two different lysis mechanisms can be distinguished depending on penetration of the proteins of either the inner membrane or the inner and outer membranes of the *E. coli*. FEMS Microbiol. Lett. 1998 Jul. 1, 164(1); 159-67 (incorporated herein by reference).

In another experiment, an active chimeric cell wall lytic enzyme (TSL) was constructed by fusing the region coding for the N-terminal half of the lactococcal phage Tuc2009 lysin and the region coding for the C-terminal domain of the major pneumococcal autolysin. The chimeric enzyme exhibited a glycosidase activity capable of hydrolysing choline-containing pneumococcal cell walls. One example of a useful fusion protein is a GST fusion protein in which the polypeptide of the disclosure is fused to the C-terminus of a GST sequence. Such a chimeric protein can facilitate the purification of a recombinant polypeptide of the disclosure.

In another embodiment, the chimeric protein or peptide contains a heterologous signal sequence at its N-terminus. For example, the native signal sequence of a polypeptide of the disclosure can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992, incorporated herein by reference). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

Another embodiment discloses an immunoglobulin fusion protein in which all or part of a polypeptide of the disclosure is fused to sequences derived from a member of the immunoglobulin protein family. An immunoglobulin fusion protein can be incorporated into a pharmaceutical composition and administered to a subject to inhibit an interaction between a ligand (soluble or membrane-bound) and a protein on the surface of a cell (receptor), to thereby suppress signal transduction in vivo. The immunoglobulin fusion protein can alter bioavailability of a cognate ligand of a polypeptide of the disclosure. Inhibition of ligand/receptor interaction may be useful therapeutically, both for treating bacterial-associated diseases and disorders for modulating (i.e. promoting or inhibiting) cell survival. Moreover, an immunoglobulin fusion protein of the disclosure can be used as an immunogen to produce antibodies directed against a polypeptide of the disclosure in a subject, to purify ligands and in screening assays to identify molecules which inhibit the interaction of receptors with ligands. Chimeric and fusion proteins and peptides of the disclosure can be produced by standard recombinant DNA techniques.

In another embodiment, the fusion gene can be synthesized by conventional techniques, including automated DNA synthesizers. Alternatively, PCR amplification of gene fragments can be carried out using anchor primers which give rise to complementary overhangs between two consecutive gene fragments which subsequently can be annealed and reamplified to generate a chimeric gene sequence (see, i.e., Ausubel et al., supra). Moreover, many expression vectors are commercially available that already encode a fusion moiety (i.e., a GST polypeptide). A nucleic acid encoding a polypeptide of the disclosure can be cloned into such an expression vector such that the fusion moiety is linked in-frame to the polypeptide of the disclosure.

As used herein, shuffled proteins or peptides, gene products, or peptides for more than one related phage protein or protein peptide fragments have been randomly cleaved and reassembled into a more active or specific protein. Shuffled oligonucleotides, peptides or peptide fragment molecules are selected or screened to identify a molecule having a desired functional property. This method is described, for example, in Stemmer, U.S. Pat. No. 6,132,970.(Method of shuffling polynucleotides); Kauffman, U.S. Pat. No. 5,976,862 (Evolution via Condon-based Synthesis) and Huse, U.S. Pat. No. 5,808,022 (Direct Codon Synthesis). The contents of these patents are incorporated herein by reference. Shuffling is used to create a protein that is 10 to 100 fold more active than the template protein. The template protein is selected among different varieties of lysin or holin proteins. The shuffled protein or peptides constitute, for example, one or more binding domains and one or more catalytic domains. Each binding or catalytic domain is derived from the same or a different phage or phage protein. The shuffled domains are either oligonucleotide based molecules, as gene or gene products, that either alone or in combination with other genes or gene products are translatable into a peptide fragment, or they are peptide based molecules. Gene fragments include any molecules of DNA, RNA, DNA-RNA hybrid, antisense RNA, Ribozymes, ESTs, SNIPs and other oligonucleotide-based molecules that either alone or in combination with other molecules produce an oligonucleotide molecule capable or incapable of translation into a peptide.

As noted above, the present disclosure discusses the use of holin proteins. Holin proteins produce holes in the cell membrane. More specifically, holins form lethal membrane lesions. Like the lytic proteins, holin proteins are coded for and carried by a phage. In fact, it is quite common for the genetic code of the holin protein to be next to or even within the code for the phage lytic protein. Most holin protein sequences are short, and overall, hydrophobic in nature, with a highly hydrophilic carboxy-terminal domain. In many cases, the putative holin protein is encoded on a different reading frame within the enzymatically active domain of the phage. In other cases, holin protein is encoded on the DNA next or close to the DNA coding for the cell wall lytic protein. Holin proteins are frequently synthesized during the late stage of phage infection and found in the cytoplasmic membrane where they cause membrane lesions.

Holins can be grouped into two general classes based on primary structure analysis. Class I holins are usually 95 residues or longer and may have three potential transmembrane domains. Class II holins are usually smaller, at approximately 65-95 residues, with the distribution of charged and hydrophobic residues indicating two TM domains (Young, et al. Trends in Microbiology v. 8, No. 4, March 2000). At least for the phages of gram-positive hosts, however, the dual-component lysis system may not be universal. Although the presence of holins has been shown or suggested for several phages, no genes have yet been found encoding putative holins for all phages. Holins have been shown to be present in several bacteria, including, for example, lactococcal bacteriophage Tuc2009, lactococcal NLC3, pneumococcal bacteriophage EJ-1, *Lactobacillus gasseri* bacteriophage Nadh, *Staphylococcus aureus* bacteriophage Twort, *Listeria monocytogenes* bacteriophages, pneumococcal phage Cp-1, *Bacillus* subtillis phage M29, *Lactobacillus* delbrueckki bacteriophage LL-H lysin, and bacteriophage N11 of Staphyloccous aureus. (Loessner, et al., Journal of Bacteriology, August 1999, p. 4452-4460).

The modified or altered form of the protein or peptides and peptide fragments, as disclosed herein, includes protein or peptides and peptide fragments that are chemically synthesized or prepared by recombinant DNA techniques, or both.

These techniques include, for example, chimerization and shuffling. When the protein or peptide is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

In one embodiment of the disclosure, a signal sequence of a polypeptide of can facilitate transmembrane movement of the protein and peptides and peptide fragments of the disclosure to and from mucous membranes, as well as by facilitating secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the disclosure can pertain to the described polypeptides having a signal sequence, as well as to the signal sequence itself and to the polypeptide in the absence of the signal sequence (i.e., the cleavage products). In one embodiment, a nucleic acid sequence encoding a signal sequence of the disclosure can be operably linked in an expression vector to a protein of interest, such as a protein which is ordinarily not secreted or is otherwise difficult to isolate. The signal sequence directs secretion of the protein, such as from an eukaryotic host into which the expression vector is transformed, and the signal sequence is subsequently or concurrently cleaved. The protein can then be readily purified from the extracellular medium by art recognized methods. Alternatively, the signal sequence can be linked to a protein of interest using a sequence which facilitates purification, such as with a GST domain.

In another embodiment, a signal sequence can be used to identify regulatory sequences, i.e., promoters, enhancers, repressors. Since signal sequences are the most amino-terminal sequences of a peptide, it is expected that the nucleic acids which flank the signal sequence on its amino-terminal side will be regulatory sequences that affect transcription. Thus, a nucleotide sequence which encodes all or a portion of a signal sequence can be used as a probe to identify and isolate the signal sequence and its flanking region, and this flanking region can be studied to identify regulatory elements therein. The present disclosure also pertains to other variants of the polypeptides of the disclosure. Such variants have an altered amino acid sequence which can function as either agonists (mimetics) or as antagonists. Variants can be generated by mutagenesis, i.e., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein. Variants of a protein of the disclosure which function as either agonists (mimetics) or as antagonists can be identified by screening combinatorial libraries of mutants, i.e., truncation mutants, of the protein of the disclosure for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (i.e., for phage display). There are a variety of methods which can be used to produce libraries of potential variants of the polypeptides of the disclosure from a degenerate oligonucleotide sequence. Methods for synthesizing degenerate oligonucleotides are known in the art (see, i.e., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477, all herein incorporated by reference).

In addition, libraries of fragments of the coding sequence of a polypeptide of the disclosure can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest. Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the disclosure (Arkin and Yourvan (1992) Proc. Natl. Acad. Sci. USA 89:7811-7815; Delgrave et al. (1993) Protein Engineering 6(3):327-331) immunologically active portions of a protein or peptide fragment include regions that bind to antibodies that recognize the phage enzyme. In this context, the smallest portion of a protein (or nucleic acid that encodes the protein) according to embodiments is an epitope that is recognizable as specific for the phage that makes the lysin protein. Accordingly, the smallest polypeptide (and associated nucleic acid that encodes the polypeptide) that can be expected to bind antibody and is useful for some embodiments may be 8, 9, 10, 11, 12, 13, 15, 20, 25, 30, 35, 40, 45, 50, 55, 60, 65, 75, 85, or 100 amino acids long. Although small sequences as short as 8, 9, 10, 11, 12 or 15 amino acids long reliably comprise enough structure to act as epitopes, shorter sequences of 5, 6, or 7 amino acids long can exhibit epitopic structure in some conditions and have value in an embodiment. Thus, the smallest portion of the protein described by SEQ ID No. 1 includes polypeptides as small as 5, 6, 7, 8, 9, or 10 amino acids long.

Homologous proteins and nucleic acids can be prepared that share functionality with such small proteins and/or nucleic acids (or protein and/or nucleic acid regions of larger molecules) as will be appreciated by a skilled artisan. Such small molecules and short regions of larger molecules, that may be homologous specifically are intended as embodiments. Preferably the homology of such valuable regions is at least 50%, 65%, 75%, 85%, and more preferably at least 90%, 95%, 97%, 98%, or at least 99% compared to SEQ ID No. 1. These percent homology values do not include alterations due to conservative amino acid substitutions.

Of course, an epitope as described herein may be used to generate an antibody and also can be used to detect binding to molecules that recognize the lysin protein. Another embodiment is a molecule such as an antibody or other specific binder that may be created through use of an epitope such as by regular immunization or by a phase display approach where an epitope can be used to screen a library if potential binders. Such molecules recognize one or more epitopes of lysin protein or a nucleic acid that encodes lysin protein. An antibody that recognizes an epitope may be a monoclonal antibody, a humanized antibody, or a portion of an antibody protein. Desirably the molecule that recognizes an epitope has a specific binding for that epitope which is at least 10 times as strong as the molecule has for serum albumin. Specific binding can be measured as affinity (Km). More desirably the specific binding is at least $10^2$, $10^3$, $10^4$, $10^5$, $10^6$, $10^7$, $10^8$, or even higher than that for serum albumin under the same conditions.

In a desirable embodiment the antibody or antibody fragment is in a form useful for detecting the presence of the lysin protein. A variety of forms and methods for their synthesis are known as will be appreciated by a skilled artisan. The antibody may be conjugated (covalently complexed) with a reporter molecule or atom such as a fluor, an enzyme that creates an optical signal, a chemilumiphore, a microparticle, or a radioactive atom. The antibody or antibody fragment may be synthesized in vivo, after immunization of an animal, for example, The antibody or antibody fragment may be synthesized via cell culture after genetic recombination. The antibody or antibody fragment may be prepared by a combination of cell synthesis and chemical modification.

Biologically active portions of a protein or peptide fragment of the embodiments, as described herein, include polypeptides comprising amino acid sequences sufficiently identical to or derived from the amino acid sequence of the phage protein of the disclosure, which include fewer amino acids than the full length protein of the phage protein and exhibit at least one activity of the corresponding full-length protein. Typically, biologically active portions comprise a domain or motif with at least one activity of the corresponding protein. A biologically active portion of a protein or protein fragment of the disclosure can be a polypeptide which is, for example, 10, 25, 50, 100 less or more amino acids in length. Moreover, other biologically active portions, in which other regions of the protein are deleted, or added can be prepared by recombinant techniques and evaluated for one or more of the functional activities of the native form of a polypeptide of the embodiments.

A large variety of isolated cDNA sequences that encode phage associated lysing enzymes and partial sequences that hybridize with such gene sequences are useful for recombinant production of the lysing enzyme. Representative nucleic acid sequences in this context are polynucleotide sequences coding for the polypeptide of SEQ ID NO:2 sequence and sequences that hybridize, under stringent conditions, with complementary sequences of the DNA of the FIG. 1 sequence. Still further variants of these sequences and sequences of nucleic acids that hybridize with those shown in Pie figures also are contemplated for use in production of lysing enzymes according to the disclosure, including natural variants that may be obtained.

Many of the contemplated variant DNA molecules include those created by standard DNA mutagenesis techniques, such as M13 primer mutagenesis. Details of these techniques are provided in Sambrook et al. (1989) In Molecular Cloning: A Laboratory Manual, Cold Spring Harbor, N.Y. (incorporated herein by reference). By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristic of the BSMR protein are contemplated by the disclosure. Also included are one small DNA molecules which are derived from the disclosed DNA molecules. Such small DNA molecules include oligonucleotides suitable for use as hybridization probes or polymerase chain reaction (PCR) primers. As such, these small DNA molecules will comprise at least a segment of a lytic enzyme genetically coded for by a bacteriophage specific for *Bacillus anthracis* and, for the purposes of PCR, will comprise at least a 10-15 nucleotide sequence and, more preferably, a 15-30 nucleotide sequence of the gene. DNA molecules and nucleotide sequences which are derived from the disclosed DNA molecules as described above may also be defined as DNA sequences which hybridize under stringent conditions to the DNA sequences disclosed, or fragments thereof.

Hybridization conditions corresponding to particular degrees of stringency vary depending upon the nature of the hybridization method of choice and the composition and length of the hybridizing DNA used. Generally, the temperature of hybridization and the ionic strength (especially the sodium ion concentration) of the hybridization buffer will determine the stringency of hybridization. Calculations regarding hybridization conditions required for attaining particular degrees of stringency are discussed by Sambrook et al. (1989), In Molecular Cloning: A Laboratory Manual, Cold Spring Harbor, N.Y., chapters 9 and 11, (herein incorporated by reference).

An example of such calculation is as follows. A hybridization experiment may be performed by hybridization of a DNA molecule (for example, a natural variation of the lytic enzyme genetically coded for by a bacteriophage specific for *Bacillus anthracis*) to a target DNA molecule. A target DNA may be, for example, the corresponding cDNA which has been electrophoresed in an agarose gel and transferred to a nitrocellulose membrane by Southern blotting (Southern (1975). J. Mol. Biol. 98:503), a technique well known in the art and described in Sambrook et al. (1989) In Molecular Cloning: A Laboratory Manual, Cold Spring Harbor, N.Y. (incorporated herein by reference). Hybridization with a target probe labeled with isotopic P (32) labeled-dCTP is carried out in a solution of high ionic strength such as 6 times SSC at a temperature that is 20-25 degrees Celsius below the melting temperature, Tm, (described infra). For such Southern hybridization experiments where the target DNA molecule on the Southern blot contains 10 ng of DNA or more, hybridization is carried out for 6-8 hours using 1-2 ng/ml radiolabeled probe (of specific activity equal to 109 CPM/mug or greater). Following hybridization, the nitrocellulose filter is washed to remove background hybridization. The washing conditions are as stringent as possible to remove background hybridization while retaining a specific hybridization signal. The term "Tm" represents the temperature above which, under the prevailing ionic conditions, the radiolabeled probe molecule will not hybridize to its target DNA molecule.

The Tm of such a hybrid molecule may be estimated from the following equation: Tm=81.5 degrees C. −16.6(log10 of sodium ion concentration)+0.41(% G+C)-0.63(% formamide)-(600/l) where l=the length of the hybrid in base pairs. This equation is valid for concentrations of sodium ion in the range of 0.01M to 0.4M, and it is less accurate for calculations of Tm in solutions of higher sodium ion concentration (Bolton and McCarthy (1962). Proc. Natl. Acad. Sci. USA 48:1390) (incorporated herein by reference). The equation also is valid for DNA having G+C contents within 30% to 75%, and also applies to hybrids greater than 100 nucleotides in length. The behavior of oligonucleotide probes is described in detail in Ch. 11 of Sambrook et al. (1989), In Molecular Cloning: A Laboratory Manual, Cold Spring Harbor, N.Y. (incorporated herein by reference). The preferred exemplified conditions described here are particularly contemplated for use in selecting variations of the lytic gene.

Thus, by way of example, of a 150 base pair DNA probe derived from the first 150 base pairs of the open reading frame of a cDNA having a % GC=45%, a calculation of hybridization conditions required to give particular stringencies may be made as follows:

Assuming that the filter will be washed in 0.3×SSC solution following hybridization, sodium ion =0.045M; % GC=45%; Formamide concentration=0 1=150 base pairs (see equation in Sambrook et al.) and so Tm=74.4 degrees C. The Tm of double-stranded DNA decreases by 1-1.5 degrees C. with every 1% decrease in homology (Bonner et al. (1973). J. Mol. Biol. 81:123). Therefore, for this given example, washing the filter in 0.3 times SSC at 59.4-64.4 degrees C. will produce a stringency of hybridization equivalent to 90%; DNA molecules with more than 10% sequence variation relative to the target BSMR cDNA will not hybridize. Alternatively, washing the hybridized filter in 0.3 times SSC at a temperature of 65.4-68.4 degrees C. will yield a hybridization stringency of 94%; DNA molecules with more than 6% sequence variation relative to the target BSMR cDNA molecule will not hybridize. The above example is given entirely by way of theoretical illustration. One skilled in the art will appreciate that other hybridization techniques may be utilized and that variations in experimental conditions will necessitate alternative calculations for stringency.

In preferred embodiments of the present disclosure, stringent conditions may be defined as those under which DNA molecules with more than 25% sequence variation (also termed "mismatch") will not hybridize. In a more preferred embodiment, stringent conditions are those under which DNA molecules with more than 15% mismatch will not hybridize, and more preferably still, stringent conditions are those under which DNA sequences with more than 10% mismatch will not hybridize. Preferably, stringent conditions are those under which DNA sequences with more than 6% mismatch will not hybridize.

The degeneracy of the genetic code further widens the scope of the embodiments as it enables major variations in the nucleotide sequence of a DNA molecule while maintaining the amino acid sequence of the encoded protein. For example, a representative amino acid residue is alanine. This may be encoded in the cDNA by the nucleotide codon triplet GCT. Because of the degeneracy of the genetic code, three other nucleotide codon triplets—GCT, GCC and GCA—also code for alanine. Thus, the nucleotide sequence of the gene could be changed at this position to any of these three codons without affecting the amino acid composition of the encoded protein or the characteristics of the protein. The genetic code and variations in nucleotide codons for particular amino acids are well known to the skilled artisan. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein comprehended by this disclosure.

One skilled in the art will recognize that the DNA mutagenesis techniques described here can produce a wide variety of DNA molecules that code for a bacteriophage lysin specific for *Bacillus anthracis* yet that maintain the essential characteristics of the lytic protein. Newly derived proteins may also be selected in order to obtain variations on the characteristic of the lytic protein, as will be more fully described below. Such derivatives include those with variations in amino acid sequence including minor deletions, additions and substitutions.

While the site for introducing an amino acid sequence variation is predetermined, the mutation per se does not need to be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions may be in single form, but preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure (EP 75,444A).

Substitutional variants are those in which at least one residue in the amino acid sequence has been removed and a different residue inserted in its place. Such substitutions may be made in accordance with the following Table 1 when it is desired to finely modulate the characteristics of the protein. Table 1 shows amino acids which may be substituted for an original amino acid in a protein and which are regarded as conservative substitutions.

TABLE 1

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |

TABLE 1-continued

| Original Residue | Conservative Substitutions |
| --- | --- |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than in Table 1, i.e., selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties will be those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the lytic protein by analyzing the ability of the derivative proteins to complement the sensitivity to DNA cross-linking agents exhibited by phages in infected bacteria hosts. These assays may be performed by transfecting DNA molecules encoding the derivative proteins into the bacteria as described above.

Having herein provided nucleotide sequences that code for lytic enzyme genetically coded for by a bacteriophage specific for *Bacillus anthracis* and fragments of that enzyme, correspondingly provided are the complementary DNA strands of the cDNA molecule and DNA molecules which hybridize under stringent conditions to the lytic enzyme cDNA molecule or its complementary strand. Such hybridizing molecules include DNA molecules differing only by minor sequence changes, including nucleotide substitutions, deletions and additions. Also contemplated by this disclosure are isolated oligonucleotides comprising at least a segment of the cDNA molecule or its complementary strand, such as oligonucleotides which may be employed as effective DNA hybridization probes or primers useful in the polymerase chain reaction. Hybridizing DNA molecules and variants on the lytic enzyme cDNA may readily be created by standard molecular biology techniques.

The detection of specific DNA mutations may be achieved by methods such as hybridization using specific oligonucleotides (Wallace et al. (1986). Cold Spring Harbor Symp. Quant. Biol. 51:257-261), direct DNA sequencing (Church and Gilbert (1988). Proc. Natl. Acad. Sci. USA 81:1991-1995), the use of restriction enzymes (Flavell et al. (1978). Cell 15:25), discrimination on the basis of electrophoretic mobility in gels with denaturing reagent (Myers and Maniatis (1986). Cold Spring Harbor Symp. Quant. Biol. 51:275-284), RNase protection (Myers et al. (1985). Science 230:1242), chemical cleavage (Cotton et al. (1985). Proc. Natl. Acad. Sci. USA 85:4397-4401) (incorporated herein by reference), and the ligase-mediated detection procedure (Landegren et al., 1988).

Oligonucleotides specific to normal or mutant sequences are chemically synthesized using commercially available machines, labeled radioactively with isotopes (such as .sup.32 P) or non-radioactively (with tags such as biotin (Ward and Langer et al. Proc. Natl. Acad. Sci. USA 78:6633-6657 1981) (incorporated herein by reference), and hybridized to individual DNA samples immobilized on membranes or other solid supports by dot-blot or transfer from gels after electrophoresis. The presence or absence of these specific sequences are visualized by methods such as autoradiography or fluorometric or colorimetric reactions (Gebeyehu et al. Nucleic Acids Res. 15:4513-4534 1987) (incorporated herein by reference).

Sequence differences between normal and mutant forms of the gene may also be revealed by the direct DNA sequencing method of Church and Gilbert (1988) (incorporated herein by reference). Cloned DNA segments may be used as probes to detect specific DNA segments. The sensitivity of this method is greatly enhanced when combined with PCR (Stoflet et al. Science 239:491-494, 1988) (incorporated herein by reference). In this approach, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent tags. Such sequences are useful for production of lytic enzymes according to embodiments of the disclosure.

Additional objects and advantages embodiments found in the disclosure will be set forth in the description which follows, and in part will be obvious from the description, or may be learned by practice of the embodiments. The objects and advantages of the disclosure may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the disclosure, and, together with the general description given above and the detailed description of the preferred embodiment given below, serve to explain the principles of the disclosure.

FIG. 1 shows the polynucleotide DNA sequence for the Gamma lysin (SEQ ID NO:1) and the corresponding amino acid sequence of the Gamma lysin (SEQ ID NO:2);

Figures 2, 3, 4:
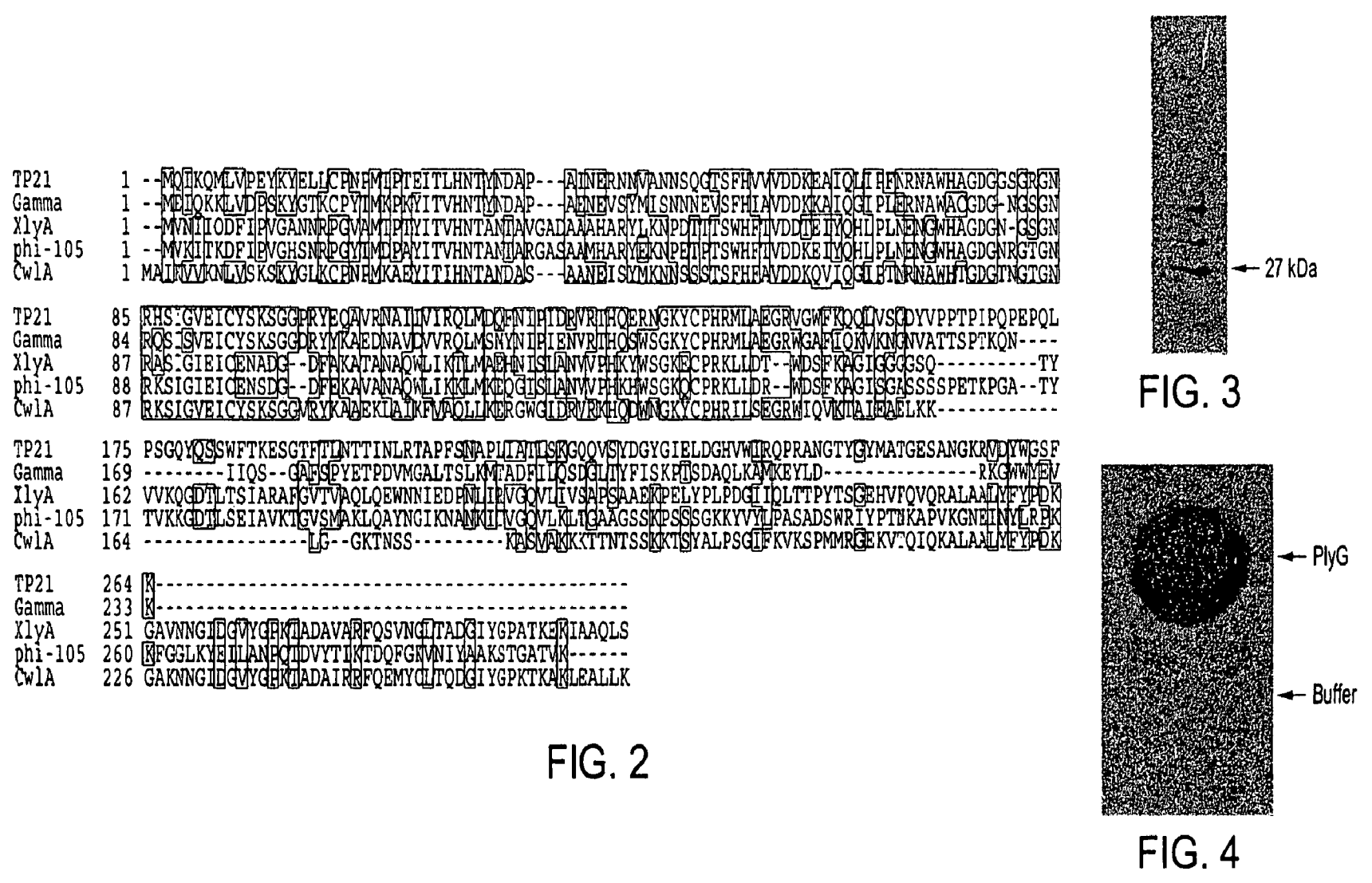

FIG. 2 is a sequence alignment of an amino acid sequence (SEQ ID NO:2) identified within the egamma lysin, PlyG, with known cell wall amidases, corresponding to SEQ ID NO:4, SEQ ID NO:6, SEQ ID NO:7 and SEQ ID NO:8.

FIG. 3 is a Coomassie Blue-stained, SDS-PAGE of purified PlyG;

FIG. 4 is a set of *Bacillus anthracis* isolates from America, Europe, Asia and Africa;

FIG. 14 is a graph showing the effect of PlyG on spore viability;

FIG. 15 is a graph showing the specific detection of germinating spores;

FIG. 16 is a graph showing the detection of germinating RSVF1 spores in a spore mixture; and FIG. 17 is a graph showing the detection of 100 RSVF1 spores after PlyG treatment.

DETAILED DESCRIPTION

Identification of the G Lysin

Figure 5:
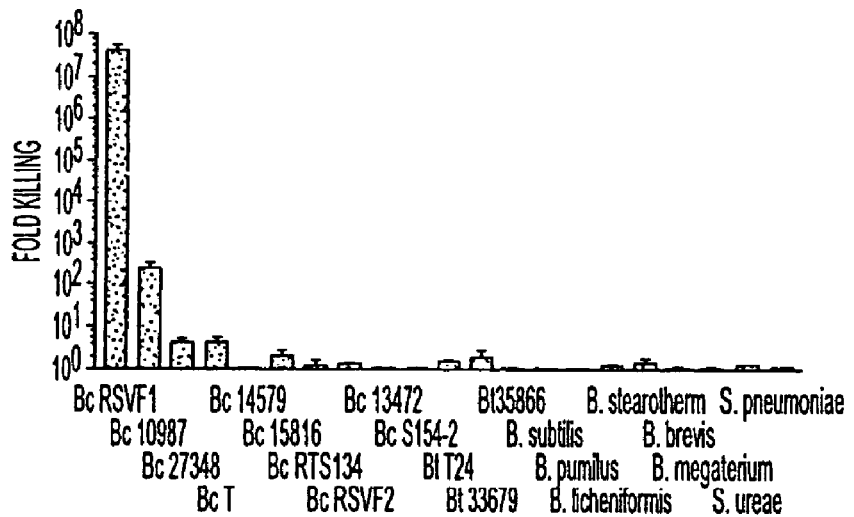
FIG. 5 is a graph showing the killing rate of the g enzyme on different strains of *bacillus;*

Referring to FIGS. 1-17, dsDNA phage of *Bacillus anthracis* form a very homogeneous family, likely reflecting the genetic uniformity of *Bacillus anthracis*. Redmond, C., Henderson, I., Turnbull, P. C. B. & Bowen, J. Phage from different strains of *Bacillus anthracis*. Salisbury Med Bull-Special Supplement 87, 60-3 (1996). The gamma phage of *Bacillus anthracis* was chosen as a lysin source since it is a standard diagnostic tool in the clinical laboratory. Brown, E. R. & Cherry, W. B. Specific identification of *Bacillus anthracis* by means of a variant bacteriophage. J Infect Dis 96, 34-9 (1955) ☐infects >85% of all *Bacillus anthracis* isolates, including some closely related but rare *B. cereus* strains that could represent virulence plasmid cured anthracis or an environmental reservoir of potential anthracis progenitors. Turnbull, P. C. B. Definitive identification of *Bacillus anthracis*—a review. J Appl Microbiol 87, 237-40 (1999).

The gamma phage was isolated from *Bacillus anthracis* and was obtained from Hans W. Ackermann (Laval University, Quebec, Canada). Phage susceptibilities were initially tested by adding 10 ml of high titer g aliquots to fresh lawns of strains indicated in Table 1; clearance after 16 h growth indicated susceptibility. A high titer phage stock containing $2.2 \times 10^{10}$ plaque forming units (pfu) ml$^{-1}$ was prepared using RSVF1 by a previously described method (Loeffler, J. M., Nelson, D. & Fischetti, V. A. Rapid killing of *Streptococcus pneumoniae* with a bacteriophage cell wall hydrolase. Science 294, 2170-2 (2001)). A pfu is a single phage that forms a small clearing zone, or plaque, after successive rounds of infection, growth, and release on lawns of susceptible bacteria. The RSVF1-derived phage stock was used in the titer determinations shown in FIG. 2.

Helgason et al. suggested such a strain in work showing that *B. cereus* RSVF1 and *Bacillus anthracis* strains are monomorphic at multiple allozyme loci and are therefore part of same cluster in the *B. cereus* lineage.

To study the specificity and strength of the gamma phage and the resulting lytic enzyme, different strains of *Bacillus* were prepared. Most strains were grown at 30° C. in Luria broth (LB) or brain-heart infusion broth (BHI), supplemented with 1.5% agar when needed. Analyses involving *E. coli* XL1-Blue (Stratagene) were performed at 37° C., while *B. stearothermophilis* was handled at 55° C. Strain RSVF1 is a streptomycin resistant derivative of *B. cereus* reference strain ATCC 4342. Despite the similarities between RSVF1 and *Bacillus anthracis*, important genotypic differences exist, and RSVF1 is not a misidentified *Bacillus anthracis* stain (Pannucci, J., Okinaka, R. T., Sabin, R. & Kuske, C. R. *Bacillus anthracis* pXO 1 plasmid sequence conservation among closely related bacterial species. J Bacteriol 184, 134-41 (2002); Helgason, E., Caugant, D. A., Olsen, I. & Kolsto, A. B. Genetic structure of population of *Bacillus cereus* and *B. thuringiensis* isolates associated with periodontitis and other human infections. J Clin Microbiol 38, 1615-22 (2000); Ticknor, L. O. et al. Fluorescent Amplified Fragment Length Polymorphism Analysis of Norwegian *Bacillus cereus* and *Bacillus thuringiensis* Soil Isolates. Appl Environ Microbiol 67, 4863-73 (2001)). Analysis of the vrrA locus of RSVF1 was performed as described (Jackson, P. J. et al. Characterization of the variable-number tandem repeats in vrrA from different *Bacillus anthracis* isolates. Appl Environ Microbiol 63, 1400-5 (1997).). *Bacillus anthracis* manipulations were provided by Leonard W. Mayer (Centers for Disease Control, Atlanta, Ga.) and Abraham L. Turetsky (Aberdeen Proving Grounds, Aberdeen, Md.). These bacterial strains were then exposed to gamma phage.

It was found that RSVF1 was sensitive to infection by g, and, as shown in FIG. 5, exhibited matt colony morphology, a filamentous structure, and repetitive sequences in the hypervariable vrrA locus which are all characteristic of *Bacillus anthracis*. The error bars of FIG. 5 indicate the standard deviation from which three to five independent experiments were performed. The lytic activity of PlyG (the gamma lysin produced by gamma phage) was examined by exposing a panel of the indicated liquid bacterial cultures to either PlyG (20 units) or phosphate buffer. The fold killing represents the decrease in bacterial viability determined 15 minutes post-lysing compared to the buffer treatment. The "Bc" and "Bt" prefixes indicate strains as either *B. cereus* or *B. thuringiensis*, respectively. RSVF1 has no virulence plasmids, but is nonetheless highly related to *Bacillus anthracis* and a suitable gamma phage host.

A phenotypic screen was used to identify gamma phage proteins that lyse RSVF1 "from without." An induced gamma phage expression library in an *E. coli* background was permeabilized and overlaid with a RSVF1 lawn. G genomic DNA was isolated using the 1 Maxi kit of Qiagen Inc. 5 mg aliquots of g DNA were partially digested with Tsp509I and cloned fragments ranging from 0.5-3.0 kb into the EcoRI site of the arabinose-inducible expression vector pBAD24. The resulting expression library was then transformed into *E. coli* XL1-Blue and screened for lysin activity on glass LB plates containing 100 mg ml$^{-1}$ ampicillin and 0.25% arabinose. The induced library was permeabilized with chloroform vapors and overlaid with exponential phase RSVF1 in 0.75% LB agar. After a 24 h incubation, distinct clearing, or lytic, zones were identified over library members. Corresponding plasmid DNA was prepared and sequenced. DNA sequence analysis and manipulations required the BLASTP (NCBI), ORF finder (NCBI), and SeqMan 5.0 (Dnastar Inc.) programs.

One of the pBAD24::plyG constructs recovered in the library search and encoding only the plyG ORF was used as a source of recombinant PlyG. Expression was induced with 0.25% L-arabinose in an overnight LB culture supplemented with ampicillin 100 mg ml$^{-1}$. Cells were washed, resuspended in 50 mM Tris, pH 8.0, and lysed with chloroform added to a concentration of 16.6%. Cellular debris and chloroform were removed by centrifugation, yielding the crude PlyG supernatant. The cationic nature of PlyG enabled it to pass through a HiTrap Q Sepharose XL column (Amersham Biosciences), which bound to most contaminants. The enzyme was further purified by application to a Mono S HR 5/5 column (Amersham Biosciences) and elution in a linear gradient containing 1 M NaCl. Active fractions were pooled and purity was assessed by gel electrophoresis and chromatography on a Superose 12 column (Amersham Biosciences) equilibrated with gel filtration standards (Bio-Rad).

Clones that yielded lytic zones all contained a 702 bp g ORF encoding a product homologous to lysins called N-acetylmuramoyl-L-alanine amidases, as shown in FIG. 2. TP21 and f 105 indicate *B. cereus* and *B. subtilis* phage amidases, respectively. CwlA and ClyA are encoded in the *B. cereus* and *B. subtillis* genomes, respectively. The dark shading represents sequence identity and the lighter shading represents similarity. Homology is restricted to their catalytic NH2-terminal halves, and absent in the lysin-specific COOH-terminal binding domains. Recombinant g lysin (called PlyG, for phage lysin gamma) was purified to homogeneity by column chromatography using Coomassie Blue-stained, SDS-Page of purified PlyG. (FIG. 3) The molecular mass was estimated based on the positions of Kaleidoscope (Bio-Rad) standards that are not shown. The N-terminal sequence of this band corresponds to the predicted PlyG sequence. Gel filtration confirmed a predicted size of ~27 kDa, and suggests that PlyG acts as a monomer and is not proteolytically processed.

In Vitro Lysin Activity

Activity was examined in several ways. A Spectramax Plus 384 spectrophotometer (Molecular Devices) was used to follow the drop in $OD_{650}$ of logarithmic phase RSVF1 incubated for 15 min at 37° C. with serial dilutions of purified PlyG. Enzyme activity in units $ml^{-1}$ was then determined as described (Nelson, D., Loomis, L. & Fischetti, V. A., Prevention and elimination of upper respiratory colonization of mice by group A streptococci by using a bacteriophage lytic enzyme. Proc Natl Acad Sci USA 98, 4107-12 (2001)). It was estimated that 1 unit of enzyme corresponded to 1 mg of PlyG. A crude measure of lysin specificity was performed in which 10 ml drops of purified PlyG (0.5 units) were applied to fresh lawns derived from the indicated strains. After overnight incubation, the appearance of clearing zones was used to assess activity. A liquid killing assay was also used, in which 1.0 ml of logarithmic phase cells (~1.0×10$^8$ cells) was treated with the indicated amounts of PlyG for 15 min at 37° C.; at the indicated time points, samples were removed, washed to remove lysin, and plated for enumeration. As a measure of PlyG-directed lysis, ATP released from dying cells was indirectly measured in a reaction containing a luciferin/luciferase reagent and a microluminometer (PROFILE-1 reagent kit and model 3550i luminometer, New Horizons Diagnostics Corp.) according to the manufacturers protocol. In brief, vegetative cells of the indicated strains were immobilized on 0.45 uM filters at the base of a 0.4 ml reaction chamber. The immobilized cells were washed twice with somatic cell releasing agent to remove impurities and 0.1 ml of PlyG in phosphate buffer was added for 2 min. 0.05 ml of the lucifierin/luciferase reagent provided with the kit was added and immediately assayed at room temperature for 10 sec. All samples were tested five times. The relative light units released by RSVF1 were consistently ten to twenty percent of its total releasable light (as determined using a strong detergent mixture provided with the kit).

RSVF1 was as sensitive to PlyG killing as a set of *Bacillus anthracis* isolates from America, Europe, Asia and Africa (13 and Table 1). *B. cereus* 10987, a rare strain closely related to *Bacillus anthracis*, was slightly susceptible to PlyG, while all other strains examined were resistant. Helgason, E. et al. *Bacillus anthracis, Bacillus cereus*, and *Bacillus thuringiensis*—one species on the basis of genetic evidence. Appl Environ Microbiol 66, 2627-30 (2000). A more sensitive test of PlyG-mediated killing was evaluated in buffer containing ~5.0×10$^7$ bacteria and treated with 20 units of PlyG for 15 min. RSVF1 was reduced >1.6×10$^7$-fold (FIG. 5), while ATCC 10987 was reduced ~100 fold. Other strains examined were largely resistant, even after a three-hour incubation. PlyG can clearly direct a potent and specific lethal action to the *Bacillus anthracis* cluster, exhibiting a substrate specificity that closely matches the gamma phage host range. Moreover, the capsulated state of several *Bacillus anthracis* strains examined, indicated that capsule does not block access of PlyG to the cell wall.

It was found that PlyG, like most lysins, is a very active enzyme. The addition of 2 units of PlyG to ~1.0×10$^4$ RSVF1 caused an immediate release of intracellular ATP (measured as light emitted by firefly luciferin/luciferase) (FIG. 6), which is consistent with a rapid lytic effect. This effect was specific for RSVF1, and was not observed in other isolates tested, therefore suggesting that the ATP release assay is a strong diagnostic tool for g-sensitive *bacilli*. In a separate kinetic analysis of RSVF1 killing, it found that as little as 2 units (or "U") of PlyG effected a 1.7×10$^4$-fold decrease in viability within 20 sec, and sterilization at 2 min, as shown in FIG. 7. Here the time course of RSVF1 killing in cultures was treated with buffer (r) or 1 unit of PlyG (TM). These values are shown as colony forming units per ml of culture determined at each time point. The corresponding $OD_{600}$ determined for the PlyG-treated sample (Î) is shown. Interestingly, the loss of culture optical density lagged behind the loss in viability, implying that killing by PlyG does not necessarily require extensive cell wall degradation.

Microscopy

Figure 10:
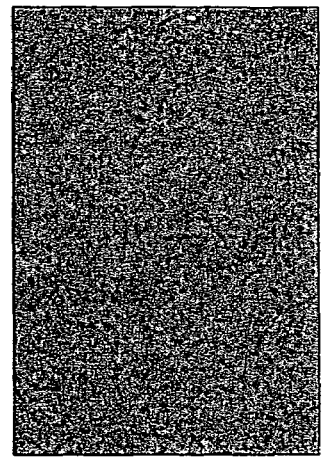
FIG. 10 is a micrograph of the RSVF1 strain of *bacillus* showing nearly complete loss of cytoplasmic material occurring 15 min after exposure to the enzyme.
Figure 11:
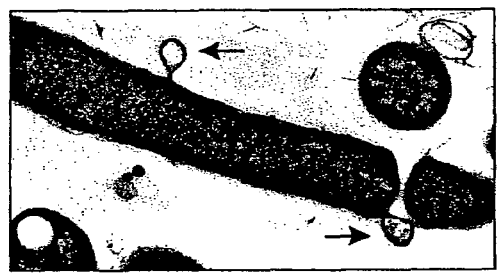
FIG. 11 is a micrograph of the rod forms of the RSVF1 strain of *bacillus* revealing the cytoplasmic membrane bulging from regions of localized cell wall hydrolysis.
Figure 12:
FIG. 12 is a micrograph of the RSVF1 strain of *bacillus* showing the rupture of the RSVF1 of the *bacillus.*

To visually examine the lytic effect phase contrast microscopy of PlyG-treated RSVF1 was used. It was found that the normally filamentous RSVF1 (FIG. 8) rapidly converts to short rod- and minicell-like forms 30 sec after exposure (FIG. 9); nearly complete loss of cytoplasmic material occurs by 15 min, leaving "ghost" cells (FIG. 10). Transmission electron microscopy of the rod forms reveals the cytoplasmic membrane bulging from regions of localized cell wall hydrolysis. These structures are usually apparent at polar and septal positions (FIG. 11), and rupture to yield a ghost-like form (FIG. 12).

In Vivo Lysin Activity

The lytic effect of PlyG suggested it could be used to kill g-sensitive bacteria in a mouse model of infection. Four- to eight-week old BALB/c female were purchased from Charles River Laboratories and housed at the Laboratory Animal Research Center at The Rockefeller University. Mouse infections were performed as a variation of a previously described procedure. Log phase RSVF1 grown in BHI medium, was pelleted and washed twice in 50 mM K·PO$_4$ buffer (pH 7.4). Aliquots of ~1.0×10$^6$ cells in buffer were injected intraperitoneally (i.p.) into mice in 0.1 ml doses. After 15 min, 0.5 ml of either buffer alone or PlyG in buffer were injected into the peritoneal cavity. Injections of PlyG alone (no bacteria) were also performed to assess toxicity. Mice were monitored for up to 3-4 days, at which time all surviving mice had recovered a normal and unremarkable appearance.

Figure 13:
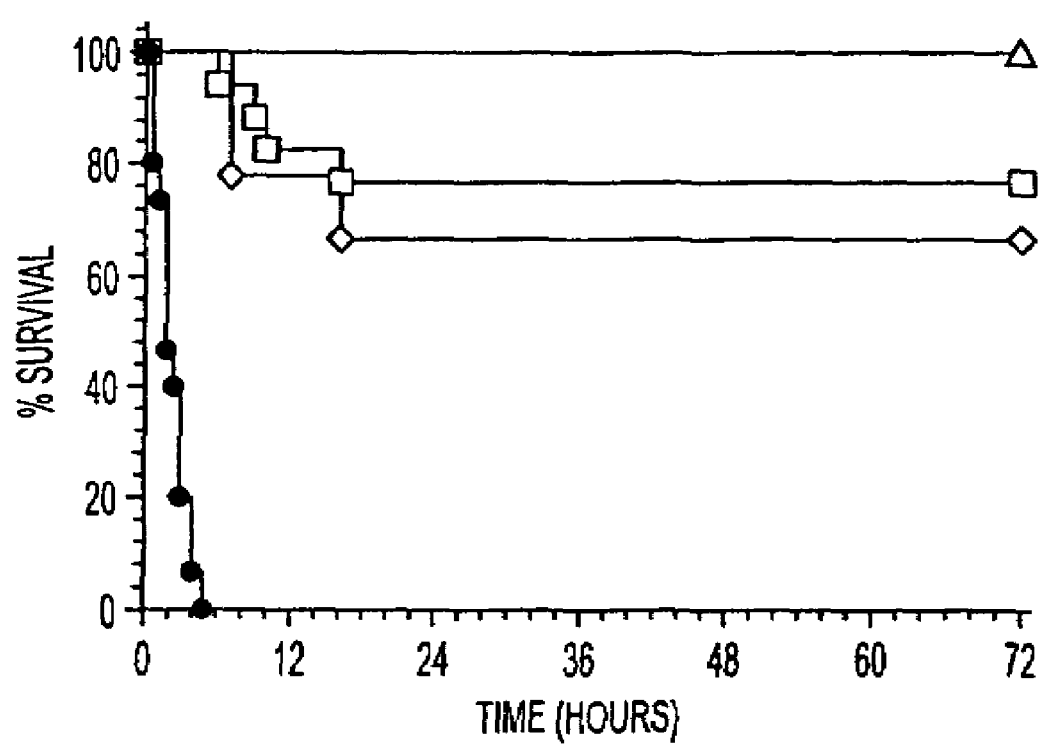
FIG. 13 is a graph showing survival of PlyG treated BALB/c mice infected with RSVF1.

The i.p. injection of some *B. cereus* isolates can induce a rapidly fatal illness similar to experimental anthrax. The injection of ~1.0×106 RSVF1 cells into BALB/c mice, killed all subjects in five hours or less (FIG. 13). More specifically, mice were injected i.p. with ~1.0×10⁶ RSVF1 cfu and treated after 15 min with either phosphate buffer (n=15), 50 U PlyG (n=17), or 150 U PlyG (n=9). As an additional control, mice that were not challenged with bacteria were injected with 50 U PlyG (n=5). The experiment was terminated at 72 hours. Administration of either 50 U or 150 U to the infected mice was significantly protective compared to the buffer control (P<0.0001). The median survival time for the buffer treated mice was 2 hours. At death, many mice exhibited severe edema at the inoculation site, and hemorrhaging through the eyes and mouth. When PlyG (50 units) was injected i.p. 15 min post-infection, a pronounced therapeutic effect was observed: thirteen of nineteen mice fully recovered, while the remainder survived six to twenty-one hours. When 150 units of PlyG were used, a similar rate of recovery was observed. No toxicity was detected with either the i.p. or i.v. injection of PlyG alone. PlyG does, therefore, rapidly kill g-sensitive bacteria in an infected animal.

The ability of PlyG to degrade germinating spores was examined next. Spores were prepared as described in Mazas, M., Martinez, S., Lopez, M., Alvarez, A. B. & Martin, R. Thermal inactivation of *Bacillus cereus* spores affected by the solutes used to control water activity of the heating medium. Int J Food Microbiol 53, 61-7 (1999). Samples containing 95-99% refractile endospores, as determined by phase contrast microscopy, were stored at 4° C. in water. For spore killing experiments, 0.2 ml aliquots of ~2.0×10⁸ spores were heat activated at 65° C. for 5 min. Samples were pelleted and suspended in 1.0 ml tryptic soy broth (TSB, Difco) containing 100 mM L-alanine (to induce germination) for 5 min at 37° C. The cells were then treated with 1.0 ml of PlyG (10 units) for 5 min at 37° C. and plated for enumeration. TSB with L-alanine is a potent inducer of germination for each spore type, converting >99% of each spore type used to heat sensitive forms within 15 min. In the presence of D-alanine, germination frequency was reduced to <10%.

For spore detection, the spore killing protocol was modified for use with a microluminometer (model 3550i, New Horizons Diagnostics Corp.). Essentially, 0.1 ml of heat-activated spores (65° C., 5 min) were immobilized on a 0.45 mM filter in the 0.4 ml reaction tube. The immobilized spores were washed twice with somatic cell releasing agent and treated with 0.15 ml TSB with 100 mM L-alanine for 5 min at room temperature. Samples were then washed and treated with 0.15 ml PlyG (2 units) for 5 min at room temperature. 50 ml of a luciferin/luciferase reagent was added for the indicated length of time and a quantitative measure of the resulting light, given as relative light units, was displayed by the luminometer. In the dormant state, the spore's peptidoglycan, or cortex, is protected from lysozymes and amidases by a proteinaceous coat. However, within 10 min of inducing germination, coat porosity increases as it begins to degrade; it was reasoned that subjacent peptidoglycan may be rendered susceptible to PlyG.

Figures 14, 15, 16, 17:
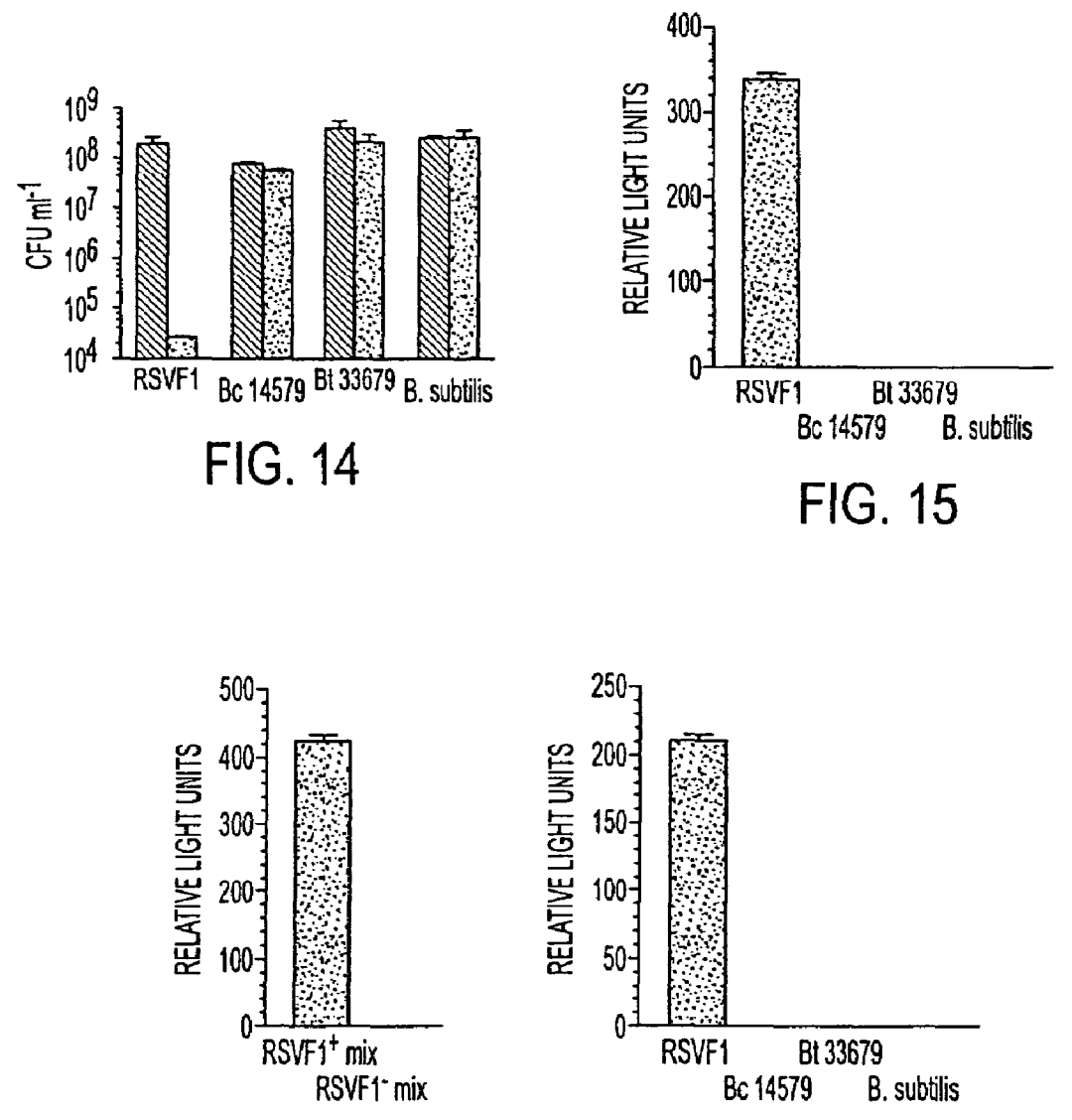

To evaluate this, spores were prepared from RSVF1, closely related *B. cereus* (ATCC 14579) and *B. thuringiensis* (ATCC 33679) strains, and *B. subtilis*. Aliquots of ~108 heat activated spores were induced to germinate for 5 min and then treated with PlyG (10 units) for 5 minutes. Resulting spore viability was compared to that of spores treated with D-alanine, a germination inhibitor (FIG. 14). While all D-alanine-treated spore samples were PlyG-resistant, only RSVF1 was sensitive after germination in the presence of L-alanine., showing a dramatic decrease in viability of log10 3.9. In FIG. 14, spores were incubated with D-alanine (hatched bars) or L-alanine (grey bars) and treated with PlyG (10 U). The D-alanine-treated spores were resistant to PlyG. Among the L-alanine-treated spores shown in FIG. 14, only RSVF1 was sensitive after induction of germination, showing a 7,500-fold decrease in viability. The resulting viability is shown. A sporocidal action, therefore, occurs rapidly after the induction of germination, when PlyG can likely access the cortex. In light of the thickness of the cortex, the rapid PlyG effect suggests a subtle alteration impairing spore outgrowth, rather than a massive degradative action.

Spore Detection

The ability of PlyG to kill germinating spores was exploited to develop a rapid and specific system for detecting g-sensitive spores using a hand-held luminometer. Spores were immobilized or placed on filters or in cuvettes (in a solution) and incubated in at least one 5 min round with at least one germinant and PlyG (2 units). The temperature at which the incubation took place was from room temperature to 60 degrees Centigrade. The spores could be incubated first in germinant and then in PlyG or with the germinant and PlyG together. The phage associated lytic enzyme does not have to be PlyG but must be specific for the spore being tested. The release of ATP from degrading spores was then measured as a light "flash" emitted in the presence of a luciferin/luciferase reagent. ATP released from PlyG-treated germinating spores was assessed in the presence of luciferin/luciferase. 2.5×10³ RSVF1 spores were induced to germinate with L-alanine and treated with 2 units of PlyG. The PlyG-mediated flash is shown in FIG. 15. FIG. 15 shows specific detection of 2.5× 10³ germinating spores. In FIG. 15, ATP released 5 min after PlyG treatment (2 U) generates the indicated light signal. Germinating spores of Bc 14579, Bt 33679, and *B. subtilis* showed no activity, demonstrating the expected recognition specificity of PlyG. Not surprisingly, when spore preparations were mixed, only the combination containing RSVF1 yielded a light signal Samples containing 2.5×10³ spores of Bc 14579, Bt 33679, and *B. subtilis* with (RSVF+mix) or without (RSVF1−mix) RSVF1 were induced to germinate in L-alanine. The intensity of luminescence after PlyG treatment (2 units) is shown in FIG. 16. FIG. 16 shows detection of RSVF1 in a spore mixture. Mixtures containing 2.5×10³ spores each of *B. cereus* (Bc) 14579, *B. thuringiensis* (Bt) 33679 and *B. subtilis* with (RSVF1+) or without (RSVF1−_RSVF1 were induced to germinate; the light release 5 minutes after PlyG treatment (2 U) is indicated in FIG. 16. The sensitivity of our system was examined using samples containing as few as ~100 spores. Rather than an immediate light flash, an RSVF1 signal was observed after 60 min incubation in the presence of PlyG and the luciferin/luciferase reagent (FIG. 17). In FIG. 17, 100 spores of the indicated types was induced to germinate, the light release 60 min. after addition of 2 U of PlyG is shown. This signal is consistent with a low-level "glow", and is consistent with the low levels of ATP likely being released. No glow was detected in the presence of other germinating spore types, and is, therefore, specific to the g-sensitive spores. This sensitivity, combined with the specificity, rapidness, and highly portable nature of our detection method, suggests applications in monitoring both domestic and battlefield use of *Bacillus anthracis* as a biological weapon. This technique may be used to identify the presence of spores from other bacterial species using bacteriophage lysins specific for those species.

The phage associated enzyme used to lyse the *Bacillus anthracis* spores may be a lytic enzyme, chimeric lytic enzymes, shuffled lytic enzymes, and combinations thereof. The phage associated lytic enzyme, and its altered forms, may be the PLY G enzyme, or another phage associated lytic enzyme specific for *Bacillus anthracis*.

A holin protein may also be used to assist in the lysing of the germinating spores. The holin protein may be unaltered, chimeric, shuffled, or may be combinations, thereof.

The nature of the luminometer that may be used for the detection of ATP, and its method of use is found and described in U.S. Pat. No. 6,395,504 (herein incorporated by reference).

Mutagenesis and Screening for PlyG Resistance

Spontaneous lysin resistance was initially examined as described (Loeffler, et al.) by repeated exposure to PlyG at low concentrations on agar plates or to increasing concentrations in liquid assays. No resistance was detected.

To determine if spontaneous resistance was at all possible, chemically mutagenized cells were examined. Log phase RSVF1 was treated for 4 hours with methanesulfonic acid ethyl ester (EMS) at a concentration of 150 mM, resulting in 90% killing. The cells were then washed with BHI and grown 3 h (three cell doublings) prior to freezing at −70° C. The efficiency of mutagenesis was estimated by the frequency of mutations giving resistance to 150 mg ml$^{-1}$ streptomycin (strep$^R$) or to 3.5 mg ml$^{-1}$ novobiocin (nov$^R$). The spontaneous frequencies in non-mutagenized cultures were $2.4 \times 10^{-9}$ for strep$^R$ and $4.0 \times 10^{-10}$ for strep$^R$; for EMS treated RSVF1 the frequencies were $2.1 \times 10^{-6}$ for strep$^R$ and $4.3 \times 10^{-6}$ for strep$^R$. For screening, frozen mutagenized cells were then thawed, washed in BHI, and grown for 30 min at 30° C. One milliliter aliquots (~$1.0 \times 10^8$ cells) were incubated with PlyG for 30 min at 37° C., washed, and either plated or incubated overnight in BHI. Colonies arising from the plated cells were picked and evaluated for resistance to 20 units of PlyG in the spectrophotometric lysin assay. For the overnight BHI cultures, log phase cells were established and ultimately treated again with PlyG as before; this was repeated for 4 successive days. In one set of experiments, 20 units of PlyG was used for each treatment, while in another 0.05 units was used and followed by serial 10-fold higher doses on following days. Bacteria were plated after each treatment, and later examined for resistance to 20 units of PlyG in the spectrophotometric lysin assay. No resistance was detected.

New Diagnostics and Therapeutics from the Gamma Phage Lysin Binding Site

The binding site of the gamma phage lysin resides in the carboxyl terminal region of the protein and is particularly valuable for the detection and therapy of anthrax.

Embodiments of the disclosure provide new proteins, nucleic acids and other molecules that can detect and/or kill anthrax due to a binding reaction between a binding protein with a sequence as taught herein. For diagnostics, the binding is accompanied by, or followed by, a detection step such as accumulation of gold sol particles, fluorescence from an attached tag, chemiluminescence from an attached tag, and the like. For killing, the binding occurs between a conjugate binding site and the bacterial wall wherein the non-binding portion of the conjugate acts to kill the bacteria, either directly or indirectly.

In such embodiments, a binding site modeled after the discovered gamma phage lysine binding site is used to direct a signaling portion or microbiocide portion to the bacteria. In embodiments for pharmaceuticals that kill the bacteria, the binding site region is coupled to a killing agent, such as an N-acetyl-muramoyl-L-alanine amidase, a glucosamimidase, a muramidase, and/or an endopeptidase. The killing agent conveniently may be taken or derived from a naturally occurring gamma phage enzyme. In embodiments for detection of the bacteria, the binding site region is coupled to a detectable agent, such as gold sol particles, selenium sol particles, a coloigenic enzyme, fluorgenic enzyme, chemiluminogenic enzyme, a fluor, a chemilumiphore, or the like. In each case, the binding site binds specifically (preferably with an affinity constant of at least $10^5$, more preferably $10^6$ and even more than $10^7$) binds to the outer surface of the bacteria. The specific binding allows both detection and killing by conjugated moieties that preferably are covalently attached to the binding site.

A wide variety of binding sites are available for targeting detection agents and therapeutic agents, as discussed next.

Natural Binding Site Region Variations

A wide variety of amino acid sequences are useful for constructing the binding site region, based on the discovery of a sequence that binds unusually well to this organism. As seen in FIG. 2, the amino terminal portion of gamma phage lysin (SEQ ID NO:2) shows high homology to the catalytic regions of TP21 (SEQ ID NO:4), XlyA (SEQ ID NO:6), phi-105(SEQ ID NO:7) and CwlA (SEQ ID NO:8). In contrast, starting from about no. 157 to residue no. 233 of SEQ ID NO:2 less sequence homology can be seen among these sequences, indicating that this region is the specific binding region that is strain and species specific. In some embodiments of the disclosure, proteins and other molecules that contain a stretch of amino acids having the sequence shown from positions 157 to 233 of SEQ ID NO:2 (the "Natural Binding Region") are very useful for detection and/or therapy of anthrax.

As depicted in FIG. 1, conservative amino acid changes to a sequence such as K with R; V, I and L with each other and W, F and Y for each other may be made while preserving at least some activity. Furthermore, unlike many proteins, the gamma phage lysin shown here binds unusually strongly with its cell surface cognate partner, with an association constant that was measured as high as $10^{11}$. Accordingly, one or more conservative amino acid changes can be made to this sequence. Even if such change decreases the binding affinity 10,000 times, the protein still binds well with an association constant of approximately $10^7$. Because of the extreme binding, in some cases, making a conservative amino acid change can improve performance by detuning the structure of the binding region to allow it to bind to a wider variety of binding partners and thus potentially respond to a wider variety of strains of anthrax that have differing wall properties.

Experimental data with a highly related organism, B. cereus showed that protein with the exact sequence shown in FIG. 1 could still react with and lyse cell walls of this bacteria. That is, the data shows that lowered binding affinity associated with amino acid modifications such as replacing 1 to 10% of the amino acids with conservative substitutions can provide advantageous properties. A contemplated property is the substitution of up to 1, 2, 5, 8, 10, 12 or 15 percent of the amino acids to broaden the range of specificity in the manner indicated by the experimental results.

In one embodiment of the disclosure, polypeptides and fragments are used that have at least a binding affinity of 10 fifth power, sixth power, seventh power, eighth power, ninth power, tenth power or even eleventh power. A molecule may be used having a homologous sequence with at least 50% sequence identity, more preferably at least 60% more preferably, at least 70% sequence identity, more preferably at least 80% sequence identity, more preferably at least 95% sequence identity, more preferably at least 97% sequence identity and even more preferably at least 98% identity to the Natural Binding Region shown in this figure. Advantages may be found when the binding site is at least 50 amino acids long, at least 60 amino acids long or at least 70 amino acids long wherein the length is homologous to the Natural Binding Region shown in the figure, although sequences of at least 8-10, 15, 20, 25, 30 and 40 amino acids, are expressly contemplated. The term "homologous to" in this context means lined up for maximum identity correspondence as seen with four sequences in Figure No. 1.

As used herein, a "fragment" is a variant polypeptide having an amino acid sequence that entirely is the same as part but not all of the amino acid sequence of the aforementioned polypeptides. A fragment may be "free-standing," or comprised within a larger polypeptide of which they form a part or region, most preferably as a single continuous region, a single larger polypeptide.

Fragments may include, for example, truncation polypeptides having a portion of an amino acid sequence corresponding to (e.g., 50% sequence identity, more preferably at least 60% more preferably, at least 70% sequence identity, more preferably at least 80% sequence identity, more preferably at least 95% sequence identity, more preferably at least 97% sequence identity and even more preferably at least or even 98% sequence identity of at least 50 amino acid long region of the Natural Binding Region when lined up as shown in the figure, or of variants thereof, such as a continuous series of residues that includes the amino terminus, or a continuous series of residues that includes the carboxyl terminus. Degradation forms of the polypeptides of this embodiment in a host cell also are advantageous. Further advantageous are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also advantageous are fragments that have binding activities of at least $10^6$, $10^7$, $10^8$ or $10^9$ against *Bacillus anthracis*, including those with a similar activity or an improved activity, or with a decreased undesirable activity. Also advantageous are conjugates of binding site and a detectable tag or bacteriocidal tag that confers such desirable clinical function whereby the binding region specifically binds to the bacterial wall, allowing detection or killing of the anthracis.

Variants that are fragments of the polypeptides of the disclosure may be employed for producing the corresponding full-length polypeptide by peptide synthesis; therefore, these variants may be employed as intermediates for producing the full-length polypeptides of embodiments of the disclosure.

Polynucleotides That Encode the Binding Site and Lysin

Another aspect of the disclosure relates to isolated polynucleotides, including the full length gene. The polynucleotides encode at least the binding site region polypeptide having a deduced amino acid sequence of the Natural Binding Region shown in FIG. 1, polynucleotides closely related thereto and variants thereof.

Using the information provided herein, a polynucleotide of the disclosure encoding a binding site region or an entire gamma lytic polypeptide may be obtained using standard cloning and screening methods. For example, cloning and sequencing chromosomal DNA fragments from bacteria using the cells infected with phage as starting material may be carried out, followed by obtaining a full length clone. To obtain a polynucleotide sequence of the disclosure, such as a sequence given in FIG. 1, typically an induced gamma phage expression library in an *E. coli* background or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence, it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., MOLECULAR CLONING, A LABORATORY MANUAL, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70).

Another embodiment of the disclosure provides a polynucleotide sequence identical over its entire length to the coding sequence in FIG. 1. Also provided by the disclosure is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro-protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the disclosure, the marker sequence is a hexa-histidine peptide, as provided in the pQE vector (Qiagen, Inc.) and described in Gentz et al., Proc. Natl. Acad. Sci., USA 86: 821-824 (1989), or an HA tag (Wilson et al., Cell 37:767 (1984). Polynucleotides of the disclosure also include, but are not limited to, polynucleotides comprising a structural gene and its naturally associated sequences that control gene expression.

Embodiments of the disclosure further include variants of the polynucleotides described herein that encode variants of the polypeptide having the deduced amino acid sequence of the Natural Binding Region. Variants that are fragments of the polynucleotides of the disclosure may be used to synthesize full-length polynucleotides of the disclosure.

Further particularly interesting features are polynucleotides encoding variants of the Natural Binding Region that have the amino acid sequence in which several, a few, 5 to 10, 1 to 5, 1 to 3, 2, 1 or no amino acid residues are substituted, deleted or added, in any combination, including silent substitutions, additions and deletions, that do not decrease binding to the *Bacillus anthracis* wall by more than a factor of 100.

Additional features of the disclosure are polynucleotides that are at least 50%, 60% or 70% identical over their entire length to a polynucleotide encoding the Natural Binding Sequence polypeptide, and polynucleotides complementary thereto. Alternatively, most highly preferred are polynucleotides that comprise a region that is at least 80% identical over its entire length to a polynucleotide encoding the binding polypeptide and polynucleotides complementary thereto. In this regard, polynucleotides at least 90% identical over their entire length to the same are particularly advantageous, and among these polynucleotides, those with at least 95% have certain advantages, as do those with at least 97% as well as those with at least 98% and at least 99%.

The disclosure further relates to polynucleotides that hybridize to the herein above-described sequences. In this regard, the disclosure especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42 degrees. C in a solution comprising: 50% formamide, 5.times.SSC (150 mM NaCl, 15 mM trisodium citrate), 50 mM sodium phosphate (pH7.6), 5.times.Denhardt's solution, 10% dextran sulfate, and 20 micrograms/ml denatured, sheared salmon sperm DNA, followed by washing the hybridization support in 0.1 times SSC at about 65 degrees C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The disclosure also provides a polynucleotide consisting essentially of a polynucleotide sequence obtainable by screening an appropriate library containing the complete gene for a polynucleotide sequence set forth herein under stringent hybridization conditions with a probe having the complementary sequence of the polynucleotide sequence set forth herein or a fragment thereof and isolating said DNA sequence. Fragments useful for obtaining such a polynucleotide include, for example, probes and primers produced from the sequences.

As discussed additionally herein regarding polynucleotide assays of the disclosure, for instance, polynucleotides of the disclosure as discussed above, may be used as a hybridization probe for RNA, cDNA and genomic DNA to isolate full-length cDNAs and genomic clones encoding the binding region and to isolate cDNA and genomic clones of other genes that have a high sequence similarity to the binding region or complete gamma lysin gene. Such probes generally will comprise at least 15 bases. Such probes could have at least 30 bases and may have at least 50 bases. Embodiments include probes having between 30 bases and 50 bases.

The polynucleotides and polypeptides of the disclosure may be employed, for example, as research reagents and materials for discovery of treatments of and diagnostics for disease, particularly human disease, as further discussed herein relating to polynucleotide assays.

Vectors, Host Cells for Expressing Gamma Lysin and Binding Site Reagents

Embodiments of the disclosure also include vectors that comprise a polynucleotide or polynucleotides of the disclosure, including just the binding region, or as much as the entire lysin protein or ligation/conjugate of binding region with other protein. Other embodiments concern host cells that are genetically engineered with vectors of the disclosure and the production of polypeptides of the disclosure by recombinant techniques. Cell-free translation systems can also be employed to produce such proteins using RNAs derived from the DNA constructs of the disclosure.

For recombinant production, host cells can be genetically engineered to incorporate expression systems or portions thereof or polynucleotides of the disclosure. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as *Streptococci, Staphylococci, Enterococci* *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3 T3, BHK, 293 and Bowes melanoma cells; and plant cells.

A great variety of expression systems can be used to produce the polypeptides of the disclosure. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the disclosure can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography is also employed for purification. Well known techniques for refolding protein may be employed to regenerate active conformation when the polypeptide is denatured during isolation and or purification.

Diagnostic Assays

Because the C-terminal binding domain of the gamma lysin is quite specific for *Bacillus anthracis*, this domain may be used as a diagnostic tool for the identification of *Bacillus anthracis*. The high affinity binding site may be used in a wide range of assay techniques to detect *Bacillus anthracis*. These techniques are well-known to those of skill in the art. Such assay methods include radioimmunoassays, gold sol radial immune assays, competitive-binding assays, Western Blot assays and ELISA assays.

Detection assays advantageously utilize a heterogeneous format wherein a binding reaction between a conjugated binding agent and an analyte occurs followed by a wash step to remove unbound conjugated binding agent. For example, gold sol particles may be prepared with protein that comprises the binding region with the binding protein immobilized on the particle surfaces. As binding occurs between the protein and bacteria, the particles merge and form a colored product. Analogously, the binding protein may be complexed, preferably covalently with an enzyme such as beta galactosidase, peroxidase, or horseradish peroxidase. After wash, the remaining bound enzyme can be detected by adding a substrate such as a fluorogenic or chemilumigenic substrate. The binding protein may be complexed with any other reagent that can make a signal such as a rare earth fluor and detected by time resolved fluorescence, a radioactive material and detected by radioactivity measurement, or a regular fluorescent tag, and detected by fluorescence.

The conjugation of the binding region with a detectable tag may be carried out by synthetic chemistry or a biological process. For example, a DNA sequence coding for the binding region or of the entire lysine protein can be linked to genetic information that encodes a detectable marker such as green fluorescent protein (GFP) or an enzyme such as alkaline phosphatase. This could be accomplished by separating the DNA for the binding domain by removing the N-terminal catalytic domain and replacing it in frame with indicator molecules such as green flourescent protein (GFP) and purifying the expressed fusion molecule for the identification of Bacillus anthracis. Since the binding domain has a similar binding affinity of an immunoglobulin G molecule, the marked binding domain will effectively identify Bacillus anthracis with little false positive activity. One also could fuse the GFP molecule or an enzyme at the 5' end of the whole lysin enzyme if necessary, by doing so the enzymatic domain will be at least partly inactivated, still allowing the binding domain to function to bind to its substrate in the bacillus cell wall.

The isolated binding domain separated from the catalytic domain may be expressed, purified and labeled using a number of fluorescent molecules such as fluorescein isothiocyanate, rhodamine isothiocyanate and others known by skilled artisans. The binding domain may be modified with biotin to allow formation of a biotin-avidin complex after the binding region adheres to the Bacillus anthracis for identification.

Other catalytic domains may be added to the binding region. As exemplified by Diaz et al. Proc. Natl. Acad. Sci. U.S.A., 87:8125 (1990) for another system, the catalytic domain may be replaced with catalytic domains from other phage lytic enzymes to cleave other bonds in the peptidoglycan cell wall of Bacillus anthracis. For example, the portion of the 5' end of the gamma lysin gene that codes for the N-terminal catalytic domain (an amidase) may be removed and replaced with the catalytic domain from phage lytic enzymes of other bacillus phage and even from phage of other gram-positive and gram-negative bacteria. These catalytic domains may be other amidases (which may have higher activity or special features), muramidases, glucamimidases, or endopeptidases, all of which, when genetically fused to the binding domain of the gamma lysin will cleave their respective bonds in the peptidoglycan of the Bacillus anthracis. In a related embodiment two or three (or more) tandem catalytic domains of different specificities may be fused (i.e., muramidases-glucamimidases-amidase) to a single gamma lysin binding domain to cleave these bonds in the Bacillus anthracis cell wall peptidoglycan producing a highly active cleaving enzyme. Navarre (Identification of a D-alanyl-glycine endopeptidase activity. J. Biol. Chem. 1999 May 28;274: 15847-56.) has shown that triple enzymatic domains may exist in bacteriophage lytic enzymes.

Various conventional linkers can be used, e.g., diisocyanates, diisothiocyanates, carbodiimides, bis-hydroxysuccinimide esters, maleimide-hydroxysuccinimide esters, glutaraldehyde and the like, preferably a selective sequential linker such as the anhydride-isothiocyante linker disclosed in U.S. Pat. No. 4,680,338.

Pharmaceuticals For Use In Treating Anthrax Infections

It was shown that the purified PlyG lysin directs a potent lytic effect in a highly specific manner; i.e., it rapidly kills members of the Bacillus anthracis cluster of related strains in the B. cereus lineage. PlyG thus is an example of an enzyme that could be used as a means to either prevent or treat inhalational anthrax infections and as a tool with which to detect Bacillus anthracis vegetative or spore forms.

There are a number of advantages to using lytic enzymes to treat bacterial infections, particularly Bacillus anthracis. The modular design of lysins, with their distinct catalytic and binding domains, makes them ideal for domain swapping experiments in which bacterial specificities and catalytic activities can be improved or adapted for use against alternate pathogens. Since the catalytic and binding targets of lysins (peptidoglycan and associated carbohydrates, respectively) are largely essential for viability, lysin resistance will be rare. Indeed, for RSVF1 no spontaneous resistance to PlyG (frequency of $<5.0 \times 10-9$) was observed. Additionally, even in chemically mutagenized RSVF1 cultures, with 103-104-fold higher mutation rates, no resistance was observed. Rather than spontaneous mutations, horizontal gene transfer would be the more likely means for developing resistance; however, considering the short vegetative lifespan of Bacillus anthracis and its extended periods of dormancy, the acquisition of PlyG resistance from heterologous loci seems remote.

Consequently, the use of the phage lytic enzymes directed against Bacillus anthracis appears to be a viable means of treating an anthrax infection of an organism, or treating anthrax contamination of an object or a surface area.

In the case of a potential contamination of a surface or an area, such as a room, the lytic enzyme directed against Bacillus anthracis may be sprayed over the entire surface of the room, and can be sprayed on the surface of any air ducts leading into, and away from, the room. The carrier for the enzyme may have a pH in the range of from about 4.0 to about 8.0, with a more optimum range of from about 5.5 to about 7.5. Additionally, the carrier should be buffered. The enzyme may function the stabilizing buffer can have a pH range between about 4.0 and about 8.0, or even between about 5.5 and about 7.5.

The stabilizing buffer should allow for the optimum activity of the lysin enzyme. The buffer may contain a reducing reagent, such as dithiothreitol. The stabilizing buffer may also be or include a metal chelating reagent, such as ethylenediaminetetracetic acid disodium salt, or it may also contain a phosphate or citrate-phosphate buffer, or any other buffer. The concentration of the active units of enzyme believed to provide for an effective amount or dosage of enzyme may be in the range of about 100 units/ml to about 500,000 units/ml of fluid. In some cases, the range of the active units per ml of fluid may be much higher. Additionally, the carrier may also include (but is not limited to) a preservative, and an antibacterial agent to keep the carrier free of bacterial organisms.

In addition to using the lytic enzyme as described by the sequence shown in FIG. 1, and with the possible substitutional variants in the above listed table, there may also be, either in addition to or as a substitute for the lytic enzyme, chimeric and shuffled lytic enzymes.

The carrier may also include L-alanine, which may assist in the germination of any Bacillus anthracis spores present.

Compositions for treating topical infections comprise an effective amount of at least one lytic enzyme produced according to this disclosure and a carrier for delivering at least one lytic enzyme to the infected skin. The mode of application for the lytic enzyme includes a number of different types and combinations of carriers which include, but are not limited to an aqueous liquid, an alcohol base liquid, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes, but is not limited to a smear, spray, a time-release patch, a liquid absorbed wipe, and combinations thereof. The lytic enzyme may be applied to a bandage either directly or in one of the other carriers. The bandages may be sold damp or dry, wherein the enzyme is in a lyophilized form on the bandage. This method of application is most effective for the treatment of infected skin.

The carriers of topical compositions may comprise semisolid and gel-like vehicles that include a polymer thickener, water, preservatives, active surfactants or emulsifiers, antioxidants, sun screens, and a solvent or mixed solvent system. U.S. Pat. No. 5,863,560 (Osborne) discusses a number of different carrier combinations which can aid in the exposure of the skin to a medicament.

Polymer thickeners that may be used include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL.R™." (B.F. Goodrich, Cleveland, Ohio), "HYPAN.R™." (Kingston Technologies, Dayton, N.J.), "NATROSOL.R™." (Aqualon, Wilmington, Del.), "KLUCEL.R™." (Aqualon, Wilmington, Del.), or "STABILEZE.R™." (ISP Technologies, Wayne, N.J.). Preferably, the gelling agent comprises between about 0.2% to about 4% by weight of the composition. More particularly, the preferred compositional weight percent range for "CARBOPOL.R™." is between about 0.5% to about 2%, while the preferred weight percent range for "NATROSOL.R™." and "KLUCEL.R™." is between about 0.5% to about 4%. The preferred compositional weight percent range for both "HYPAN.R™." and "STABILEZE.R™." is between about 0.5% to about 4%.

"CARBOPOL.R™." is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL.R™." is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

Preservatives may also be used in this invention and preferably comprise about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Titanium dioxide may be used as a sunscreen to serve as prophylaxis against photosensitization. Alternative sun screens include methyl cinnamate. Moreover, BHA may be used as an antioxidant, as well as to protect ethoxydiglycol and/or dapsone from discoloration due to oxidation. An alternate antioxidant is BHT.

Pharmaceuticals for use in all embodiments of this disclosure include antimicrobial agents, anti-inflammatory agents, antiviral agents, local anesthetic agents, corticosteroids, destructive therapy agents, antifungals, and antiandrogens. Active pharmaceuticals that may be used in topical formulations include antimicrobial agents, especially those having anti-inflammatory properties such as dapsone, erythromycin, minocycline, tetracycline, clindamycin, and other antimicrobials. The preferred weight percentages for the antimicrobials are 0.5% to 10%.

Local anesthetics include tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate, and pramoxine hydrochloride. A preferred concentration for local anesthetics is about 0.025% to 5% by weight of the total composition. Anesthetics such as benzocaine may also be used at a preferred concentration of about 2% to 25% by weight.

Corticosteroids that may be used include betamethasone dipropionate, fluocinolone actinide, betamethasone valerate, triamcinolone actinide, clobetasol propionate, desoximetasone, diflorasone diacetate, amcinonide, flurandrenolide, hydrocortisone valerate, hydrocortisone butyrate, and desonide are recommended at concentrations of about 0.01% to 1.0% by weight. Preferred concentrations for corticosteroids such as hydrocortisone or methylprednisolone acetate are from about 0.2% to about 5.0% by weight.

Destructive therapy agents such as salicylic acid or lactic acid may also be used. A concentration of about 2% to about 40% by weight is preferred. Cantharidin is preferably utilized in a concentration of about 5% to about 30% by weight. Typical antifungals that may be used in topical compositions and their preferred weight concentrations include: oxiconazole nitrate (0.1% to 5.0%), ciclopirox olamine (0.1% to 5.0%), ketoconazole (0.1% to 5.0%), miconazole nitrate (0.1% to 5.0%), and butoconazole nitrate (0.1% to 5.0%). Other topical agents may be included to address a variety of topical co-infections that may occur as will be appreciated by skilled artisans.

Typically, treatments using a combination of drugs include antibiotics in combination with local anesthetics such as polymycin B sulfate and neomycin sulfate in combination with tetracaine for topical antibiotic gels to provide prophylaxis against infection and relief of pain. Another example is the use of minoxidil in combination with a corticosteroid such as betamethasone dipropionate for the treatment of alopecia ereata. The combination of an anti-inflammatory such as cortisone with an antifungal such as ketoconazole for the treatment of tinea infections is also an example.

In one embodiment, the invention comprises a dermatological composition having about 0.5% to 10% carbomer and about 0.5% to 10% of a pharmaceutical that exists in both a dissolved state and a micro particulate state. The dissolved pharmaceutical has the capacity to cross the stratum corneum, whereas the micro particulate pharmaceutical does not. Addition of an amine base, potassium, hydroxide solution, or sodium hydroxide solution completes the formation of the gel. More particularly, the pharmaceutical may include dapsone, an antimicrobial agent having anti-inflammatory properties. A preferred ratio of micro particulate to dissolved dapsone is five or less.

In another embodiment, the invention comprises about 1% carbomer, about 80-90% water, about 10% ethoxydiglycol, about 0.2% methylparaben, about 0.3% to 3.0% dapsone including both micro particulate dapsone and dissolved dapsone, and about 2% caustic material. More particularly, the carbomer may include "CARBOPOL.R™. 980" and the caustic material may include sodium hydroxide solution.

In a preferred embodiment, the composition comprises dapsone and ethoxydiglycol, which allows for an optimized ratio of micro particulate drug to dissolved drug. This ratio determines the amount of drug delivered, compared to the amount of drug retained in or above the stratum corneum to function in the supracorneum domain. The system of dapsone and ethoxydiglycol may include purified water combined with "CARBOPOL.R™." gelling polymer, methylparaben, propylparaben, titanium dioxide, BHA, and a caustic material to neutralize the "CARBOPOL.R™."

Any of the carriers for the lytic enzyme may be manufactured by conventional means. However, if alcohol is used in the carrier, the enzyme should be in a micelle, liposome, or a "reverse" liposome, to prevent denaturing of the enzyme. Similarly, when the lytic enzyme is being placed in the carrier, and the carrier is, or has been heated, such placement should be made after the carrier has cooled somewhat, to avoid heat denaturation of the enzyme. In a preferred embodiment of the invention, the carrier is sterile.

The enzyme may be added to these substances in a liquid form or in a lyophilized state, whereupon it will be solubilized when it meets a liquid body.

When treating an anthrax exposure or infection, the lytic enzyme may be administered preferably, either parenterally or through the oral or nasal cavity.

Compositions which may be used for the prophylactic and therapeutic treatment of a *Bacillus anthracis* infection includes the shuffled and/or chimeric enzyme and a means of application (such as a carrier system or an oral delivery mode) to the mucosal lining of the oral and nasal cavity, such that the enzyme is put in the carrier system or oral delivery mode to reach the mucosa lining.

Prior to, or at the time the modified lytic enzyme is put in the carrier system or oral delivery mode, it is the enzyme may be in a stabilizing buffer environment for maintaining a pH range between about 4.0 and about 8.0, or more exacting, between about 5.0 and about 7.0.

The stabilizing buffer should allow for the optimum activity of the lysin enzyme. The buffer may contain a reducing reagent, such as dithiothreitol. The stabilizing buffer may also be or include a metal chelating reagent, such as ethylenediaminetetracetic acid disodium salt, or it may also contain a phosphate or citrate-phosphate buffer, or any other buffer. The DNA coding of these phages and other phages may be altered to allow a recombinant enzyme to attack one cell wall at more than two locations, to allow the recombinant enzyme to cleave the cell wall of more than one species of bacteria, to allow the recombinant enzyme to attack other bacteria, or any combinations thereof. The type and number of alterations to a recombinant bacteriophage produced enzyme are incalculable. Any number of chimeric and shuffled lytic enzymes, alone or along with holin proteins, may be assembled to treat the exposure to *Bacillus anthracis*.

For example, if there is a bacterial infection of the upper respiratory tract, the infection can be prophylactically or therapeutically treated with a composition comprising an effective amount of at least one lytic enzyme produced by a bacteria being infected with a bacteriophage specific for that bacteria, and a carrier for delivering the lytic enzyme to a mouth, throat, or nasal passage. The lytic enzyme may be a lytic enzyme, a chimeric lytic enzyme, and/or shuffled lytic enzyme which may be used in conjunction with a holin protein or a combination thereof. The lytic enzyme may be in an environment having a pH which allows for activity of the lytic enzyme. The optimum pH range for this enzyme is about 4-8 with a pH of about 6-7 being the most optimal. If an individual has been exposed to someone with the upper respiratory disorder, the lytic enzyme will reside in the mucosal lining and prevent any colonization of the infecting bacteria.

Means of application of the lytic enzyme(s) (modified or unmodified) include, but are not limited to direct, indirect, carrier and special means or any combination of means. Direct application of the lytic enzyme may be by nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or any combination of these and similar methods of application. The forms in which the lytic enzyme may be administered include but are not limited to lozenges, troches, candies, injectants, chewing gums, tablets, powders, sprays, liquids, ointments, and aerosols. It is most probable that exposure to the *Bacillus anthracis* will be through the nose. It is best to be treated for exposure to the bacteria as soon as possible.

When the lytic enzyme(s) is introduced directly by use of nasal sprays, nasal drops, nasal ointments, nasal washes, nasal injections, nasal packing, bronchial sprays, oral sprays, and inhalers, the enzyme is preferably in a liquid or gel environment, with the liquid acting as the carrier. A dry anhydrous version of the modified enzyme may be administered by the inhaler and bronchial spray, although a liquid form of delivery is preferred.

The lozenge, tablet, or gum into which the enzyme is added may contain sugar, corn syrup, a variety of dyes, non-sugar sweeteners, flavorings, any binders, or combinations thereof. Similarly, any gum based products may contain acacia, carnauba wax, citric acid, corn starch, food colorings, flavorings, non-sugar sweeteners, gelatin, glucose, glycerin, gum base, shellac, sodium saccharin, sugar, water, white wax, cellulose, other binders, and combinations thereof.

Lozenges may further contain sucrose, corn starch, acacia, gum tragacanth, anethole, linseed, oleoresin, mineral oil, and cellulose, other binders, and combinations thereof. In another embodiment of the disclosure, sugar substitutes are used in place of dextrose, sucrose, or other sugars.

As noted above, the enzyme may also be placed in a nasal spray, wherein the spray is the carrier. The nasal spray can be a long acting or timed release spray, and can be manufactured by means well known in the art. An inhalant may also be used, so that the enzyme may reach further down into the bronchial tract, including into the lungs.

Any of the carriers for the lytic enzyme may be manufactured by conventional means. However, it is preferred that any mouthwash or similar type products not contain alcohol to prevent denaturing of the enzyme, although enzymes in liposomes and in other protective modes and forms may be used in alcohol. Similarly, when the enzyme(s) is (are) being placed in a cough drop, gum, candy or lozenge during the manufacturing process, such placement should be made prior to the hardening of the lozenge or candy but after the cough drop or candy has cooled somewhat, to avoid heat denaturation of the enzyme. The enzyme can also be sprayed over the surface of the cough drop gum, candy, or lozenge, in high enough dosages to be effective.

The enzyme may be added to these substances in a liquid form or in a lyophilized state, whereupon it will be solubilized when it meets body fluids such as saliva. The enzyme may also be in a micelle or liposome.

The effective dosage rates or amounts of the enzyme(s) to treat the infection will depend in part on whether the enzyme(s) will be used therapeutically or prophylactically, the duration of exposure of the recipient to the infectious bacteria, the size and weight of the individual, etc. The duration for use of the composition containing the enzyme also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of enzyme that may provide for an effective amount or dosage of enzyme may be in the range of about (e.g. exactly) 100 units/ml to about 500,000 units/ml of fluid in the wet or damp environment of the nasal and oral passages, and topically as well and possibly in the range of about 100 units/ml to about 50,000 units/ml. Representative values thus include about 200 units/ml, 300 units/ml, 500 units/ml, 1,000 units/ml, 2,500 units/ml, 5,000 units/ml, 10,000 units/ml, 20,000 units/ml, 30,000 units/ml, and 40,000 units/ml. More specifically, time exposure to the active enzyme units may influence the desired concentration of active enzyme units per ml. It should be noted that carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depends on the nature of infection, whether treatment is to be prophylactic or therapeutic, and other variables. Thus, the number of dosages will be dependent upon the circumstances and can range from 1-4 times per day or more, with durations from one day to multiple weeks. Infections can occur in the skin and thus such compositions may be formulated for topical application as well, using well known vehicles such as those described in U.S. Pat. Nos. 6,056,954 and 6,056,955.

Most *Bacillus anthracis* infections occur when the bacterium, normally in the form of a spore, is inhaled into the nose. There, the spore can be inhaled further into the body, and into the lung, where, through a series of steps, it can germinate and lead to a systemic infection and death. Consequently, it is important to treat the infection as soon as possible, preferably while it is still in the nasal or oral cavity. When treating the infection, the carrier should further comprise a germinant, preferably L-alanine, so that the lytic enzyme (and/or the chimeric and/or shuffled lytic enzymes) can be most effective.

In another embodiment, a mild surfactant in an amount effective to potentiate the therapeutic effect of the modified lytic enzyme may be used. Suitable mild surfactants include, inter alia, esters of polyoxyethylene sorbitan and fatty acids (Tween series), octylphenoxy polyethoxy ethanol (Triton-X series), n-Octyl-beta.D-glucopyranoside, n-Octyl-betaD-thioglucopyranoside, n-Decal-beta-D-glucopyranoside, n-Dodecyl-betaD-glucopyranoside, and biologically occurring surfactants, e.g., fatty acids, glycerides, monoglycerides, deoxycholate and esters of deoxycholate. While this treatment, as with all of the other treatments, may be used in any mammalian species or any animal species that can contract or transmit anthrax, the most common use of this product may be for a human during biological warfare or terrorism.

As noted above, the lytic enzyme, and the chimeric and/or shuffled lytic enzymes, or their peptide fragments are directed to the mucosal lining, where, in residence, they kill colonizing disease bacteria. The mucosal lining, as disclosed and described herein, includes, for example, the upper and lower respiratory tract, eye, buccal cavity, nose, rectum, vagina, periodontal pocket, intestines and colon. Due to natural eliminating or cleansing mechanisms of mucosal tissues, conventional dosage forms are not retained at the application site for any significant length of time.

For these and other reasons it is advantageous to have materials which exhibit adhesion to mucosal tissues, to be administered with one or more phage enzymes and other complementary agents over a period of time. Materials having controlled release capability are particularly desirable, and the use of sustained release mucoadhesives has received a significant degree of attention.

J. R. Robinson (U.S. Pat. No. 4,615,697, incorporated herein by reference) provides a review of the various controlled release polymeric compositions used in mucosal drug delivery. The patent describes a controlled release treatment composition which includes a bioadhesive and an effective amount of a treating agent. The bioadhesive is a water swellable, but water insoluble fibrous, crosslinked, carboxy functional polymer containing (a) a plurality of repeating units of which at least about 80 percent contain at least one carboxyl functionality, and (b) about 0.05 to about 1.5 percent crosslinking agent substantially free from polyalkenyl polyether. While the polymers of Robinson are water swellable but insoluble, they are crosslinked, not thermoplastic, and are not as easy to formulate with active agents, and into the various dosage forms, as the copolymer systems of the present application. Micelles and multi lamellar micelles may also be used to control the release of enzyme.

Other approaches involving mucoadhesives which are the combination of hydrophilic and hydrophobic materials, are known. Orahesive.R™. from E.R. Squibb & Co is an adhesive which is a combination of pectin, gelatin, and sodium carboxymethyl cellulose in a tacky hydrocarbon polymer, for adhering to the oral mucosa. However, such physical mixtures of hydrophilic and hydrophobic components eventually fall apart. In contrast, the hydrophilic and hydrophobic domains in the present disclosure produce an insoluble copolymer.

U.S. Pat. No. 4,948,580, also incorporated by reference, describes a bioadhesive oral drug delivery system. The composition includes a freeze-dried polymer mixture formed of the copolymer poly(methyl vinyl ether/maleic anhydride) and gelatin, dispersed in an ointment base, such as mineral oil containing dispersed polyethylene. U.S. Pat. No. 5,413,792 (incorporated herein by reference) discloses paste-like preparations comprising (A) a paste-like base comprising a polyorganosiloxane and a water soluble polymeric material which are preferably present in a ratio by weight from 3:6 to 6:3, and (B) an active ingredient. U.S. Pat. No. 5,554,380 claims a solid or semisolid bioadherent orally ingestible drug delivery system containing a water-in-oil system having at least two phases. One phase comprises from about 25% to about 75% by volume of an internal hydrophilic phase and the other phase comprises from about 23% to about 75% by volume of an external hydrophobic phase, wherein the external hydrophobic phase is comprised of three components: (a) an emulsifier, (b) a glyceride ester, and (c) a wax material.

U.S. Pat. No. 5,942,243 describes some representative release materials useful for administering antibacterial agents according to embodiments of the disclosure.

An embodiment of a features therapeutic compositions containing polymeric mucoadhesives consisting essentially of a graft copolymer comprising a hydrophilic main chain and hydrophobic graft chains for controlled release of biologically active agents. The graft copolymer is a reaction product of (1) a polystyrene macromonomer having an ethylenically unsaturated functional group, and (2) at least one hydrophilic acidic monomer having an ethylenically unsaturated functional group. The graft chains consist essentially of polystyrene, and the main polymer chain of hydrophilic monomeric moieties, some of which have acidic functionality. The weight percent of the polystyrene macromonomer in the graft copolymer is between about 1 and about 20% and the weight percent of the total hydrophilic monomer in the graft copolymer is between 80 and 99%, and wherein at least 10% of said total hydrophilic monomer is acidic, said graft copolymer when fully hydrated having an equilibrium water content of at least 90%.

Compositions containing the copolymers gradually hydrate by sorption of tissue fluids at the application site to yield a very soft jelly like mass exhibiting adhesion to the mucosal surface. During the period of time the composition is adhering to the mucosal surface, it provides sustained release of the pharmacologically active agent, which is absorbed by the mucosal tissue.

Mucoadhesivity of the compositions of these embodiments are, to a large extent, produced by the hydrophilic acidic monomers of the chain in the polystyrene graft copolymer. The acidic monomers include, but are not limited to, acrylic and methacrylic acids, 2-acrylamido-2-methyl-propane sulfonic acid, 2-sulfoethyl methacrylate, and vinyl phosphonic acid. Other copolymerizable monomers include, but are not limited to N,N-dimethylacrylamide, glyceryl methacrylate, polyethylene glycol monomethacrylate, etc.

The compositions of the disclosure may optionally contain other polymeric materials, such as poly(acrylic acid), poly,-(vinyl pyrrolidone), and sodium carboxymethyl cellulose plasticizers, and other pharmaceutically acceptable excipients in amounts that do not cause a deleterious effect upon mucoadhesivity of the composition. The dosage forms of the compositions of this disclosure can be prepared by conventional methods.

In order to accelerate treatment of the infection, the therapeutic agent may further include at least one complementary agent which can also potentiate the bactericidal activity of the lytic enzyme. The complementary agent can be erythromycin, clarithromycin, azithromycin, roxithromycin, other members of the macrolide family, penicillins, cephalosporins, and any combinations thereof in amounts which are effective to synergistically enhance the therapeutic effect of the lytic enzyme. Virtually any other antibiotic may be used with the modified lytic enzyme. Similarly, other lytic enzymes may be included in the carrier to treat other bacterial infections. Holin proteins may be included in the therapeutic treatment.

Once the *Bacillus anthracis* gets past the nasal oral cavity, the likelihood of a systemic infection increases. Thus, it becomes necessary for the infection to be treated parenterally.

The enzymes which can be used are, as above, lytic enzymes, chimeric lytic, enzymes, shuffled lytic enzymes, and combinations thereof. The enzymes can be administered intramuscularly, intravenously, subcutaneously, subdermally, or combinations thereof. Intravenous treatment is most likely the best treatment for an full blown anthrax infection.

In one embodiment, infections may be treated by injecting into the patient a therapeutic agent comprising the appropriate shuffled and/or chimeric lytic enzyme(s) and a carrier for the enzyme. The carrier may be comprised of distilled water, a saline solution, albumin, a serum, or any combinations thereof. More specifically, solutions for infusion or injection may be prepared in a conventional manner, e.g. with the addition of preservatives such as p-hydroxybenzoates or stabilizers such as alkali metal salts of ethylene-diamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non-aqueous vehicles such as fixed oils, liposomes, and ethyl oleate are also useful herein. Other phage associated lytic enzymes, along with a holin protein, may be included in the composition.

In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are used. Stabilizers include gelatin and albumin. In some embodiments, a vasoconstriction agent is added to the formulation. The pharmaceutical preparations are provided sterile and pyrogen free. Generally, as noted above, intravenous injection may be most appropriate.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

Glycerin or glycerol (1,2,3-propanetriol) is commercially available for pharmaceutical use. It may be diluted in sterile water for injection, or sodium chloride injection, or other pharmaceutically acceptable aqueous injection fluid, and used in concentrations of 0.1 to 100% (v/v), preferably 1.0 to 50% more preferably about 20%.

DMSO, is an aprotic solvent with a remarkable ability to enhance penetration of many locally applied drugs. DMSO may be diluted in sterile water for injection, or sodium chloride injection, or other pharmaceutically acceptable aqueous injection fluid, and used in concentrations of 0.1 to 100% (v/v).

The vehicle may also include Ringer's solution, a buffered solution, and dextrose solution, particularly when an intravenous solution is prepared.

Prior to, or at the time the enzyme is put in the carrier system or oral delivery mode, it may be desirable for the enzymes be in a stabilizing buffer environment, maintaining a pH range between about 4.0 and about 8.0, more preferably between about 6.5 and about 7.5.

The stabilizing buffer should allow for the optimum activity of the enzyme. The buffer may be a reducing reagent, such as dithiothreitol. The stabilizing buffer may also be or include a metal chelating reagent, such as ethylenediaminetetracetic acid disodium salt, or it may also contain a phosphate or citrate-phosphate buffer. The buffers found in the carrier can serve to stabilize the environment for the lytic enzymes.

The effective dosage rates or amounts of the enzyme to be administered parenterally, and the duration of treatment will depend in part on the seriousness of the infection, the weight of the patient, the duration of exposure of the recipient to the infectious bacteria, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of enzyme believed to provide for an effective amount or dosage of enzyme may be in the range of about 100 units/ml to about 10,000,000 units/ml of composition, in a range of about 1000 units/ml to about 10,000,000 units/ml, and from about 10,000 to 10,000,000 units/ml. The amount of active units per ml and the duration of time of exposure depends on the nature of infection, and the amount of contact the carrier allows the lytic enzyme to have. It is to be remembered that the enzyme works best when in a fluid environment. Hence, effectiveness of the enzyme is in part related to the amount of moisture trapped by the carrier. The concentration of the enzyme for the treatment is dependent upon the bacterial count in the blood and the blood volume.

In order to accelerate treatment of the infection, the therapeutic agent may further include at least one complementary agent which can also potentiate the bactericidal activity of the lytic enzyme. The complementary agent can be any antibiotic effective against *Bacillus anthracis*. Similarly, other lytic enzymes may be included to treat other bacterial infections.

Additionally, a number of methods can be used to assist in transporting the enzyme across the cell membrane. The enzyme can be transported in a liposome, with the enzyme be "inserted" in the liposomes by known techniques. Similarly, the enzyme may be in a reverse micelle. The enzyme can also be pegylated, attaching the polyethylene glycol to the non-active part of the enzyme. Alternatively, hydrophobic molecules can be used to used to transport the enzyme across the cell membrane. Finally, the glycosylation of the enzyme can be used to target specific internalization receptors on the membrane of the cell.

For the purposes of pharmaceutical use, the lysin may be produced by any number of different methods. The lytic enzyme is produced by infecting said *Bacillus anthracis* with the genetic code delivered by a bacteriophage specific for said *Bacillus anthracis*. In another embodiment of the disclosure, the lytic enzyme is produced by recombinant production from a nucleic acid that comprises a DNA having the sequence of bases of a polynucleotide sequence coding for SEQ ID No. 1 or a sequence that hybridizes with the complement of bases of a polynucleotide sequence coding for SEQ ID No. 1 under stringent hybridization conditions. The lytic enzyme may be produced by removing a gene for the lytic enzyme from the phage genome, introducing said gene into a transfer vector, and cloning said transfer vector into an expression system., wherein the transfer vector is a plasmid. The expression system may be a bacteria, selected from any of the above listed groups, or, most preferably, from the group consisting of *E. coli* and *Bacillus*.

In another expression system production of the enzyme is by cell free expression system.

The embodiments disclosed here are not limited to the use of the gamma phage or the PlyG lytic enzyme. Indeed, any lytic enzyme genetically coded for by a bacteriophage which is specific for *Bacillus anthracis* and for and which itself is specific for *Bacillus anthracis*, may be used to identify and treat *Bacillus anthracis*.

Additionally, other specific phage associated lytic enzymes specific for other bacteria may be included with a composition containing or comprising any phage associated lytic enzyme specific for *Bacillus anthracis*.

All cited references are incorporated herein.

EXAMPLES

The following examples provide illustrations of certain embodiments of the invention.

1. Strains of Bacteria Useful With Certain Embodiments

Most strains of bacteria were grown at 30° C. in Luria broth (LB) or brain-heart infusion broth (BHI). *B. anthracis* was grown on sheep blood agar (trypticase soy base, or TSB) with or without $CO_2$ atmosphere. Work with *E. coli* XL-1 Blue (Stratagene) and *B. anthracis* was performed at 37° C., whereas *b. stearothernophilis* was handled at 55° C. RSVF1, except for the absence of virulence plasmids, is nearly indistinguishable from *B. anthracis*. See, Helgason, E, Caugant, D. A., Olsen, I and Kolsto, AB, "Genetic structure of population of *Bacillus cereus* and *B. thurigeniesis* isolates associated with periodontitis and other human infections," J. Clin. Microbiol, 38, 1615-1622 (2000); Panucci, J et al, "*Bacillus anthracis* pXO1 plasmid sequence conservation among closely related bacterial species," J. Bacteriol., 184, 134-141 (2002); Ticknor, L. O. et al, "Fluorescent amplified fragment length polymorphism analysis of Norwegian *Bacillus cereus* and *Bacillus thurigiensis* soil isolates," Appl. Environ. Microbiol, 67, 4863-4873 (2001). The vrrA locus and motility of RSVF1 were analyzed as described in Schuch, Raymond et al., "A bacteriolytic agent that detects and kills *Bacillus anthracis*," *Nature,* 418, 884-889 (Aug. 22, 2002). The susceptibility of *B. anthracis* to PlyG was examined by L. W. Mayer (CDC) and Abraham L. Turetsky (Aberdeen Proving Grounds, Md., USA).

2. Virus Manipulations Useful With Certain Embodiments

The γ phage was obtained from H. W. Ackermann. Susceptibilities were initially tested using drops of about $10^7$ phages applied to fresh lawns of the indicated strains. A phage stock containing 2.2×1010 plaque-forming units (PFU) per ml was prepared on RSVF1 as described in Schuch, Raymond et al., "A bacteriolytic agent that detects and kills *Bacillus anthracis,*" *Nature,* 418, 884-889 (Aug. 22, 2002), and used for titre determinations of susceptibility to γ-phage infection and purified PlyG activity.

3. Identification of Gamma (γ) Lysin

Partially digested 5-μg aliquots of g DNA with TSP509 I were used, and 0.5-3.0 kilobase fragments were cloned into the arabinose-inducible expression vector pBAD24. Schuch, Raymond et al., "A bacteriolytic agent that detects and kills *Bacillus anthracis,*" *Nature,* 418, 884-889 (Aug. 22, 2002). The library was transformed into *E. coli* and screened for lysin activity in a manner derived from a protocol discussed by Loessner, MJ et al., "Heterogeneous endolysins in *Listeria monocytogenes* bacteriophages: a new class of enzymes and evidence for conserved holin genes within the siphoviral lysin cassettes," Mol. Micropbiol., 16, 1231-1241 (1995). The expression library was replica plated on to glass plates with LB containing 0.25% L-arabinose and 100 μg/ml ampicillin. After overnight incubation at 37° C., the plates were inverted over lids containing 5 ml of chloroform to permeabilize the library. After 5 min., the library was overlain with 3 ml of 0.75% LB soft agar containing 300 μl of tenfold-concentrated log-phase culture of RSVF1 and incubated for 24 h. Clear lytic zones appeared at the periphery of lysin-encoding library members.

4. Protein Purification

PlyG was induced from XL1-Blue/pBAD24::plyG with 0.25% L-arabinose in overnight LB cultures. Cells were washed, resuspended in 50 mM Tris buffer at pH 8.0, and lysed with chloroform to yield crude PlyG. PlyG, which passed through a HiTrap Q Sepharose XL column (Amersham Bioscience), bound to a Mono S HR 5/5 column (Amersham Biosciences) and was eluted in a linear gradient containing 1M NaCl. Analysis of the N-terminal protein sequence confirmed the identity of PlyG.

5. In Vitro Lysin Activity

Activity was examined in different ways. First, to obtain data from FIG. 5, 1 ml of log-phase cultures were treated with either PlyG (20 U) or phosphate buffer for 15 min. Fold killing is the number of viable bacterial after buffer treatment divided by the number after PlyG treatment. In FIG. 5, "Bc" and "Bt" indicate *B. cereus* and *B. thuringiensis*, respectively.

Figure 6:
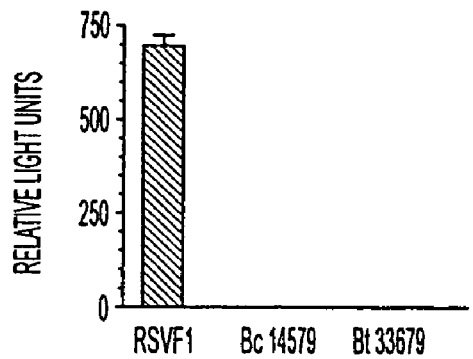
FIG. 6 is a graph showing the immediate release of intracellular ATP (measured as light emitted by firefly luciferin/luciferase) caused by the g enzyme lysing the RSVF1 strain of *bacillus;*
Figure 7:
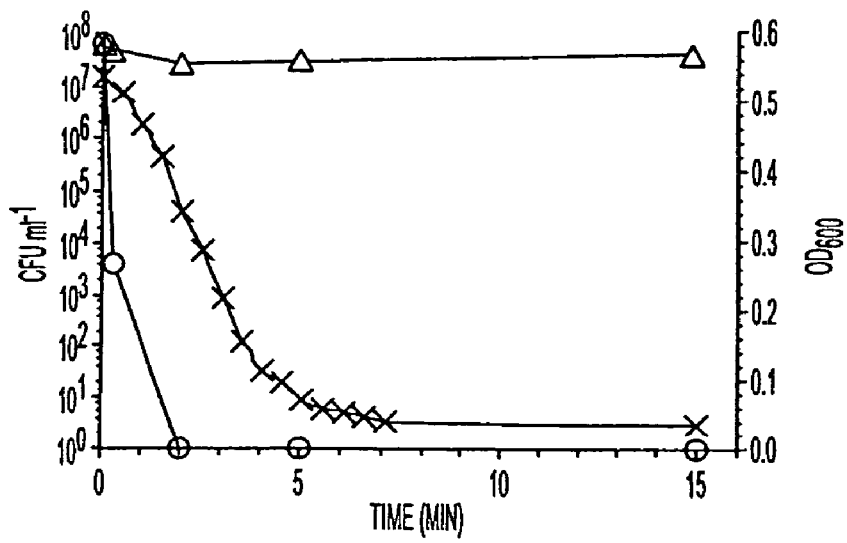
FIG. 7 is a graph showing kinetic analysis of RSVF1 killing.
Figure 8:
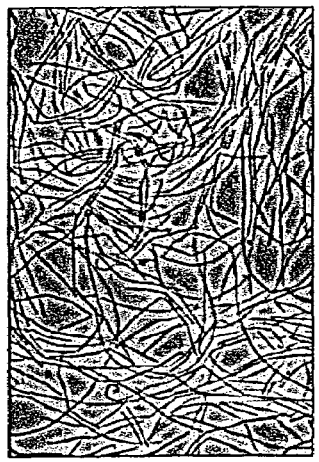
FIG. 8 is a micrograph of the normally filamentous RSVF1 strain of *bacillus;*
Figure 9:
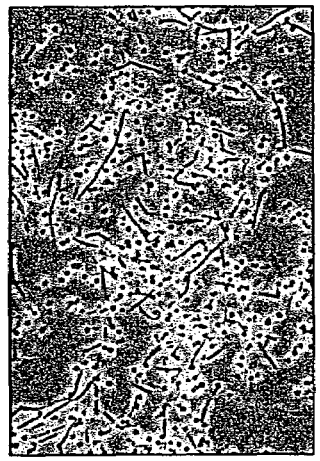
FIG. 9 is a micrograph of the RSVF1 strain of *bacillus* showing short rod- and minicell-like forms 30 sec after exposure to the lytic enzyme.

Second, to obtain the data from FIG. 6, an ATP release assay was performed using a PROFILE-1 reagent kit and model 3550i microluminometer (New Horizons Diagnostics). Use of this system, and detailed validation studies are referenced in Schuch, Raymond et al., "A bacteriolytic agent that detects and kills *Bacillus anthracis*," *Nature*, 418, 884-889 (Aug. 22, 2002). In brief, filter-immobilized vegetative bacteria were treated with 2 U of PlyG in 150 µL for 2 min; a luciferin/luciferase reagent (50 µL) was then added and light release was assayed in a 10-s integration. Relative light units (RLU) produced by RSVF1 were consistently 10-20% of total releasable light, determined using a detergent mix that releases all intracellular ATP. Total RLU was similar for each sample. The correlation between RSVF1 concentration and RLU was performed as described looking at total ATP release, as referenced in Schuch, Raymond et al., "A bacteriolytic agent that detects and kills *Bacillus anthracis*," *Nature*, 418, 884-889 (Aug. 22, 2002).

Third, to obtain the data from FIG. 7, a Spectramax Plus 384 spectrophotometer (Molecular Devices) followed the drop of absorbance at 600 nm ($A_{600}$) of log-phase (see Schuch, Raymond et al., "A bacteriolytic agent that detects and kills *Bacillus anthracis*," *Nature*, 418, 884-889 (Aug. 22, 2002)), using lysis of exponentially growing RSVF1 with serial dilutions of PlyG. 1 U corresponded to 1 μg of PlyG. For the liquid killing assay, 1.0 ml of log-phase cells was treated with various amounts of PlyG at 37° C. and, at specific time points, samples were washed to remove lysin and plated for enumeration.

6. Mutagenesis and Screening for PlyG Resistance

RSVF1 was treated with EMS as referenced in Schuch, Raymond et al., "A bacteriolytic agent that detects and kills *Bacillus anthracis*," *Nature*, 418, 884-889 (Aug. 22, 2002). Mutagenized cells were incubated with 20 U PlyG for 30 min at 37° C., washed, and either plated or incubated overnight in BHI liquid. Colonies arising from plated cells were evaluated spectrophotometrically for resistance to 20 U of PlyG. For overnight BHI cultures, log-phase cells were established and treated with PlyG as above; this sequence was repeated over 5 days using either 20 U PlyG at each treatment or increasing amounts of PlyG (0.5-50 U).

Spontaneous lysin resistance was examined as described in Schuch, Raymond et al., "A bacteriolytic agent that detects and kills *Bacillus anthracis*," *Nature*, 418, 884-889 (Aug. 22, 2002). Spontaneous and EMS-induced mutation frequencies were estimated by determining resistance to 150 μg/ml streptomycin or to 3.5 μg/ml novobiocin.

7. Microscopy

Treatment of 1 ml of log-phase RSVF1 with 5 U of PlyG was performed at various intervals as discussed above. For phase contrast microscopy, cells were viewed with an Eclipse E400 microscope (Nikon). For electron microscopy, cells were examined as described in Schuch, Raymond et al., "A bacteriolytic agent that detects and kills *Bacillus anthracis*," *Nature*, 418, 884-889 (Aug. 22, 2002). Examples of microscopy images include FIGS. 8-12.

8. In Vivo Lysin Activity

To obtain data for FIG. 13, Female BALB/c mice 4-8 weeks old were infected as referenced in Schuch, Raymond et al., "A bacteriolytic agent that detects and kills *Bacillus anthracis*," *Nature*, 418, 884-889 (Aug. 22, 2002). An i.p. injection was performed on the mice with 0.1 ml aliquots of $1.0\times10^{6}$ log-phase RSVF1 in 50 mM potassium phosphate buffer at pH 7.4. After 15 min, 0.5 ml of buffer or PlyG in buffer were injected i.p. Injections of PlyG alone (no bacteria) were also performed to assess toxicity. Mice were then monitored for 3-4 days.

9. Spore Preparation and Germination

Results from tests of PlyG-mediated spore killing and detection are provided in FIGS. 14-17. Samples containing 95-99% spores were prepared as referenced in Schuch, Raymond et al., "A bacteriolytic agent that detects and kills *Bacillus anthracis*," *Nature*, 418, 884-889 (Aug. 22, 2002). Aliquots of $2.0\times10^{8}$ spores in about 100 μL PBS were heat activated at 65° C. for 5 min and suspended in 1.0 ml tryptic soy broth (TSB) with 100 mM L-alanine (an L-alanine assay) or D-alanine (a D-alanine assay) for 5 min at 37° C. Samples were then treated with 10 U of PlyG for 5 min, washed three times (to remove residual PlyG) and plated for counting. TSB with L-alanine induced more than 99% germination, whereas D-alanine blocked germination.

For spore detection, the germinating spore-killing protocol was modified for use with the model 3550i microluminometer. Filter-immobilized, heat-activated spores in water were treated with 100 μl TSB and 100 mM L-alanine for 5 min, and 150 μl PlyG (2 U) for a further 5 min. Luciferin/luciferase (50 μl) was added and RLU were determined at certain time points. When PlyG or the germinant was omitted, no light signal was detected. When PlyG was replaced with a strong detergent mix, and total ATP was released, similar RLU were observed for equivalent numbers of each germinating spore type.

Many modifications and variations of the present disclosure are possible in light of the above teachings. Such other modifications and variations which will be readily apparent to a skilled are included within the spirit and scope of the attached claims. In the appended claims, articles such as "a," "an" and "the" may mean one or more than one unless indicated to the contrary. Claims that include "or" between one or more members of a group shall be deemed satisfied if one, more than one, or all of the group members are employed in a given product or process.

We claim:

1. A method for treating an infection comprising the step of administering to a subject a composition comprising an isolated polypeptide, the isolated polypeptide comprising the amino acid sequence of SEQ ID NO:2.

2. The method of claim 1, wherein the composition further comprises a shuffled lytic enzyme, a chimeric lytic enzyme, the polypeptide of SEQ ID NO:4, the polypeptide of SEQ ID NO:6, the polypeptide of SEQ ID NO: 7, the polypeptide of SEQ ID NO: 8, or a combination thereof.

3. The method of claim 1, wherein the composition further comprises a holin protein specific for *B. anthracis*.

4. The method of claim 1, wherein the composition further comprises a carrier.

5. The method of claim 1, wherein the composition further comprises a suitable vehicle for delivery of a lytic enzyme to an infection.

6. The method of claim 1, wherein the composition further comprises an antibiotic.

7. The method of claim 1, where the isolated polypeptide further comprises at least one polypeptide selected from the group consisting of: SEQ ID NO:3, SEQ ID NO:4, SEQ ID NO:5, SEQ ID NO:6, SEQ ID NO:7, and SEQ ID NO:8.

8. The method of claim 1, where the isolated polypeptide is a fusion protein.

9. The method of claim 8, where the fusion protein is a GST fusion protein or an immunoglobulin fusion protein.

10. The method of claim 1, where the isolated polypeptide is a shuffled lytic enzyme or a chimeric lytic enzyme.

11. The method of claim 4, where the carrier has a pH in the range of 4.0 to 8.0.

12. The method of claim 1, where the composition is administered parenterally, topically, or through the oral or nasal cavity.

13. The method of claim 1, where the isolated polypeptide consists of the amino acid sequence of SEQ ID NO:2 and the composition is administered at a dose of 100 to 500,000 units of the isolated polypeptide per ml of composition.

14. A method for treating an infection comprising the step of contacting a composition comprising the lytic enzyme of SEQ ID NO: 2 with a *Bacillus anthracis* spore.

15. The method of claim 14, wherein the composition further comprises a holin protein.

16. The method of claim 14, wherein the *Bacillus anthracis* spore is contacted with at least 2 units of the lytic enzyme.

17. The method of claim 14, wherein the composition comprises about 50-150 mg of the lytic enzyme.

18. The method of claim 14, where the composition further comprises L-alanine.

19. A method for treating an infection comprising the step of administering a composition comprising an isolated polypeptide consisting of the amino acid sequence of SEQ ID NO:2.

20. The method of claim 19, wherein the composition further comprises a holin protein.

* * * * *

SEQUENCE LISTING

```
<160> NUMBER OF SEQ ID NOS: 8

<210> SEQ ID NO 1
<211> LENGTH: 702
<212> TYPE: DNA
<213> ORGANISM: Bacillus anthracis
<220> FEATURE:
<221> NAME/KEY: CDS
<222> LOCATION: (1)..(699)
```

```
<400> SEQUENCE: 1 atg gaa atc caa aaa aaa tta gtt gat cca agt aag tat ggt aca aag      48
Met Glu Ile Gln Lys Lys Leu Val Asp Pro Ser Lys Tyr Gly Thr Lys
1               5                   10                  15 tgt ccg tat aca atg aag cct aaa tat atc act gtt cac aac aca tat      96
Cys Pro Tyr Thr Met Lys Pro Lys Tyr Ile Thr Val His Asn Thr Tyr
                20                  25                  30 aat gat gct cca gct gaa aat gaa gtg agt tac atg att agt aac aat     144
Asn Asp Ala Pro Ala Glu Asn Glu Val Ser Tyr Met Ile Ser Asn Asn
            35                  40                  45 aat gag gtg tcg ttt cat att gca gta gat gac aag aaa gcg att caa     192
Asn Glu Val Ser Phe His Ile Ala Val Asp Asp Lys Lys Ala Ile Gln
        50                  55                  60 ggt att ccg ttg gaa cgt aat gca tgg gct tgc gga gac ggc aat ggt     240
Gly Ile Pro Leu Glu Arg Asn Ala Trp Ala Cys Gly Asp Gly Asn Gly
65                  70                  75                  80 tcg ggg aat cgt caa tcc att tct gta gaa atc tgt tat tca aaa tca     288
Ser Gly Asn Arg Gln Ser Ile Ser Val Glu Ile Cys Tyr Ser Lys Ser
                85                  90                  95 gga gga gat aga tac tat aaa gct gag gat aat gct gtt gat gtt gta     336
Gly Gly Asp Arg Tyr Tyr Lys Ala Glu Asp Asn Ala Val Asp Val Val
            100                 105                 110 cga caa ctt atg tct atg tac aat att ccg att gaa aat gtt cga act     384
Arg Gln Leu Met Ser Met Tyr Asn Ile Pro Ile Glu Asn Val Arg Thr
        115                 120                 125 cat caa tcc tgg tca ggt aaa tat tgt ccg cat aga atg tta gct gag     432
His Gln Ser Trp Ser Gly Lys Tyr Cys Pro His Arg Met Leu Ala Glu
    130                 135                 140 gga agg tgg gga gca ttc att cag aag gtt aag aat ggg aat gtg gcg     480
Gly Arg Trp Gly Ala Phe Ile Gln Lys Val Lys Asn Gly Asn Val Ala
145                 150                 155                 160 act act tca cca aca aaa caa aac atc atc caa tca ggg gct ttc tca     528
Thr Thr Ser Pro Thr Lys Gln Asn Ile Ile Gln Ser Gly Ala Phe Ser
                165                 170                 175 ccg tat gaa acc cct gat gtt atg gga gca tta acg tca ctt aaa atg     576
Pro Tyr Glu Thr Pro Asp Val Met Gly Ala Leu Thr Ser Leu Lys Met
            180                 185                 190 aca gct gat ttt atc tta caa tcg gat gga tta act tat ttt att tcc     624
Thr Ala Asp Phe Ile Leu Gln Ser Asp Gly Leu Thr Tyr Phe Ile Ser
        195                 200                 205 aaa ccg act tca gat gca caa cta aaa gca atg aaa gaa tac ctt gac     672
Lys Pro Thr Ser Asp Ala Gln Leu Lys Ala Met Lys Glu Tyr Leu Asp
    210                 215                 220 cgt aaa ggt tgg tgg tat gaa gtt aaa taa                             702
Arg Lys Gly Trp Trp Tyr Glu Val Lys
225                 230

<210> SEQ ID NO 2
<211> LENGTH: 233
<212> TYPE: PRT
<213> ORGANISM: Bacillus anthracis

<400> SEQUENCE: 2

Met Glu Ile Gln Lys Lys Leu Val Asp Pro Ser Lys Tyr Gly Thr Lys
1               5                   10                  15

Cys Pro Tyr Thr Met Lys Pro Lys Tyr Ile Thr Val His Asn Thr Tyr
                20                  25                  30

Asn Asp Ala Pro Ala Glu Asn Glu Val Ser Tyr Met Ile Ser Asn Asn
            35                  40                  45
```

```
Asn Glu Val Ser Phe His Ile Ala Val Asp Asp Lys Lys Ala Ile Gln
 50                  55                  60

Gly Ile Pro Leu Glu Arg Asn Ala Trp Ala Cys Gly Asp Gly Asn Gly
 65                  70                  75                  80

Ser Gly Asn Arg Gln Ser Ile Ser Val Glu Ile Cys Tyr Ser Lys Ser
                 85                  90                  95

Gly Gly Asp Arg Tyr Tyr Lys Ala Glu Asp Asn Ala Val Asp Val Val
                100                 105                 110

Arg Gln Leu Met Ser Met Tyr Asn Ile Pro Ile Glu Asn Val Arg Thr
                115                 120                 125

His Gln Ser Trp Ser Gly Lys Tyr Cys Pro His Arg Met Leu Ala Glu
                130                 135                 140

Gly Arg Trp Gly Ala Phe Ile Gln Lys Val Lys Asn Gly Asn Val Ala
145                 150                 155                 160

Thr Thr Ser Pro Thr Lys Gln Asn Ile Ile Gln Ser Gly Ala Phe Ser
                165                 170                 175

Pro Tyr Glu Thr Pro Asp Val Met Gly Ala Leu Thr Ser Leu Lys Met
                180                 185                 190

Thr Ala Asp Phe Ile Leu Gln Ser Asp Gly Leu Thr Tyr Phe Ile Ser
                195                 200                 205

Lys Pro Thr Ser Asp Ala Gln Leu Lys Ala Met Lys Glu Tyr Leu Asp
                210                 215                 220

Arg Lys Gly Trp Trp Tyr Glu Val Lys
225                 230

<210> SEQ ID NO 3
<211> LENGTH: 233
<212> TYPE: PRT
<213> ORGANISM: Bacillus anthracis

<400> SEQUENCE: 3

Met Glu Ile Gln Lys Lys Leu Val Asp Pro Ser Lys Tyr Gly Thr Lys
  1               5                  10                  15

Cys Pro Tyr Thr Met Lys Pro Lys Tyr Ile Thr Val His Asn Thr Tyr
                 20                  25                  30

Asn Asp Ala Pro Ala Glu Asn Glu Val Ser Tyr Met Ile Ser Asn Asn
                 35                  40                  45

Asn Glu Val Ser Phe His Ile Ala Val Asp Asp Lys Lys Ala Ile Gln
 50                  55                  60

Gly Ile Pro Leu Glu Arg Asn Ala Trp Ala Cys Gly Asp Gly Asn Gly
 65                  70                  75                  80

Ser Gly Asn Arg Gln Ser Ile Ser Val Glu Ile Cys Tyr Ser Lys Ser
                 85                  90                  95

Gly Gly Asp Arg Tyr Tyr Lys Ala Glu Asp Asn Ala Val Asp Val Val
                100                 105                 110

Arg Gln Leu Met Ser Met Tyr Asn Ile Pro Ile Glu Asn Val Arg Thr
                115                 120                 125

His Gln Ser Trp Ser Gly Lys Tyr Cys Pro His Arg Met Leu Ala Glu
                130                 135                 140

Gly Arg Trp Gly Ala Phe Ile Gln Lys Val Lys Asn Gly Asn Val Ala
145                 150                 155                 160

Thr Thr Ser Pro Thr Lys Gln Asn Ile Ile Gln Ser Gly Ala Phe Ser
                165                 170                 175

Pro Tyr Glu Thr Pro Asp Val Met Gly Ala Leu Thr Ser Leu Lys Met
                180                 185                 190
```

```
Thr Ala Asp Phe Ile Leu Gln Ser Asp Gly Leu Thr Tyr Phe Ile Ser
            195                 200                 205

Lys Pro Thr Ser Asp Ala Gln Leu Lys Ala Met Lys Glu Tyr Leu Asp
    210                 215                 220

Arg Lys Gly Trp Trp Tyr Glu Val Lys
225                 230

<210> SEQ ID NO 4
<211> LENGTH: 263
<212> TYPE: PRT
<213> ORGANISM: Bacillus anthracis

<400> SEQUENCE: 4

Met Gln Ile Lys Gln Met Leu Val Pro Glu Tyr Lys Tyr Glu Leu Leu
1               5                   10                  15

Cys Pro Asn Pro Met Thr Pro Thr Glu Ile Thr Leu His Asn Thr Tyr
            20                  25                  30

Asn Asp Ala Pro Ala Ile Asn Glu Arg Asn Asn Val Ala Asn Asn Ser
        35                  40                  45

Gln Gly Thr Ser Phe His Val Val Asp Asp Lys Glu Ala Ile Gln
    50                  55                  60

Leu Ile Pro Phe Asn Arg Asn Ala Trp His Ala Gly Asp Gly Gly Ser
65                  70                  75                  80

Gly Arg Gly Asn Arg His Ser Ile Gly Val Glu Ile Cys Tyr Ser Lys
                85                  90                  95

Ser Gly Gly Pro Arg Tyr Glu Gln Ala Val Arg Asn Ala Ile Ile Val
            100                 105                 110

Ile Arg Gln Leu Met Asp Gln Phe Asn Ile Pro Ile Asp Arg Val Lys
        115                 120                 125

Thr His Gln Glu Arg Asn Gly Lys Tyr Cys Pro His Arg Met Leu Ala
    130                 135                 140

Glu Gly Arg Val Gly Trp Phe Lys Gln Gln Leu Val Ser Gly Asp Tyr
145                 150                 155                 160

Val Pro Pro Thr Pro Ile Pro Gln Pro Glu Pro Gln Leu Pro Ser Gly
                165                 170                 175

Gln Tyr Asp Ser Ser Trp Phe Thr Lys Glu Ser Gly Thr Phe Thr Leu
            180                 185                 190

Asn Thr Thr Ile Asn Leu Arg Thr Ala Pro Phe Ser Asn Ala Pro Leu
        195                 200                 205

Ile Ala Thr Leu Ser Lys Gly Gln Gln Val Ser Tyr Asp Gly Tyr Gly
    210                 215                 220

Ile Glu Leu Asp Gly His Val Trp Ile Arg Gln Pro Arg Ala Asn Gly
225                 230                 235                 240

Thr Tyr Gly Tyr Met Ala Thr Gly Glu Ser Ala Asn Gly Lys Arg Val
                245                 250                 255

Asp Tyr Trp Gly Ser Phe Lys
            260

<210> SEQ ID NO 5
<211> LENGTH: 233
<212> TYPE: PRT
<213> ORGANISM: Bacillus anthracis

<400> SEQUENCE: 5

Met Glu Ile Gln Lys Lys Leu Val Asp Pro Ser Lys Tyr Gly Thr Lys
1               5                   10                  15
```

```
Cys Pro Tyr Thr Met Lys Pro Lys Tyr Ile Thr Val His Asn Thr Tyr
             20                  25                  30

Asn Asp Ala Pro Ala Glu Asn Glu Val Ser Tyr Met Ile Ser Asn Asn
         35                  40                  45

Asn Glu Val Ser Phe His Ile Ala Val Asp Asp Lys Lys Ala Ile Gln
     50                  55                  60

Gly Ile Pro Leu Glu Arg Asn Ala Trp Ala Cys Gly Asp Gly Asn Gly
 65                  70                  75                  80

Ser Gly Asn Arg Gln Ser Ile Ser Val Glu Ile Cys Tyr Ser Lys Ser
                 85                  90                  95

Gly Gly Asp Arg Tyr Tyr Lys Ala Glu Asp Asn Ala Val Asp Val Val
            100                 105                 110

Arg Gln Leu Met Ser Met Tyr Asn Ile Pro Ile Glu Asn Val Arg Thr
            115                 120                 125

His Gln Ser Trp Ser Gly Lys Tyr Cys Pro His Arg Met Leu Ala Glu
        130                 135                 140

Gly Arg Trp Gly Ala Phe Ile Gln Lys Val Lys Asn Gly Asn Val Ala
145                 150                 155                 160

Thr Thr Ser Pro Thr Lys Gln Asn Ile Ile Gln Ser Gly Ala Phe Ser
                165                 170                 175

Pro Tyr Glu Thr Pro Asp Val Met Gly Ala Leu Thr Ser Leu Lys Met
            180                 185                 190

Thr Ala Asp Phe Ile Leu Gln Ser Asp Gly Leu Thr Tyr Phe Ile Ser
        195                 200                 205

Lys Pro Thr Ser Asp Ala Gln Leu Lys Ala Met Lys Glu Tyr Leu Asp
    210                 215                 220

Arg Lys Gly Trp Trp Tyr Glu Val Lys
225                 230

<210> SEQ ID NO 6
<211> LENGTH: 297
<212> TYPE: PRT
<213> ORGANISM: Bacillus anthracis

<400> SEQUENCE: 6

Met Val Asn Ile Ile Gln Asp Phe Ile Pro Val Gly Ala Asn Asn Arg
 1               5                  10                  15

Pro Gly Tyr Ala Met Thr Pro Ile Tyr Ile Thr Val His Asn Thr Ala
             20                  25                  30

Asn Thr Ala Val Gly Ala Asp Ala Ala Ala His Ala Arg Tyr Leu Lys
         35                  40                  45

Asn Pro Asp Thr Thr Thr Ser Trp His Phe Thr Val Asp Asp Thr Glu
     50                  55                  60

Ile Tyr Gln His Leu Pro Leu Asn Glu Asn Gly Trp His Ala Gly Asp
 65                  70                  75                  80

Gly Asn Gly Ser Gly Asn Arg Ala Ser Ile Gly Ile Glu Ile Cys Glu
                 85                  90                  95

Asn Ala Asp Gly Asp Phe Ala Lys Ala Thr Ala Asn Ala Gln Trp Leu
            100                 105                 110

Ile Lys Thr Leu Met Ala Glu His Asn Ile Ser Leu Ala Asn Val Val
            115                 120                 125

Pro His Lys Tyr Tyr Ser Gly Lys Glu Cys Pro Arg Lys Leu Leu Asp
        130                 135                 140

Thr Trp Asp Ser Phe Lys Ala Gly Ile Gly Gly Gly Ser Gln Thr
```

```
                145                 150                 155                 160
Tyr Val Val Lys Gln Gly Asp Thr Leu Thr Ser Ile Ala Arg Ala Phe
                    165                 170                 175
Gly Val Thr Val Ala Gln Leu Gln Glu Trp Asn Asn Ile Glu Asp Pro
                180                 185                 190
Asn Leu Ile Arg Val Gly Gln Val Leu Ile Val Ser Ala Pro Ser Ala
                    195                 200                 205
Ala Glu Lys Pro Glu Leu Tyr Pro Leu Pro Asp Gly Ile Ile Gln Leu
                    210                 215                 220
Thr Thr Pro Tyr Thr Ser Gly Glu His Val Phe Gln Val Gln Arg Ala
225                 230                 235                 240
Leu Ala Ala Leu Tyr Phe Tyr Pro Asp Lys Gly Ala Val Asn Asn Gly
                    245                 250                 255
Ile Asp Gly Val Tyr Gly Pro Lys Thr Ala Asp Ala Val Ala Arg Phe
                    260                 265                 270
Gln Ser Val Asn Gly Leu Thr Ala Asp Gly Ile Tyr Gly Pro Ala Thr
                    275                 280                 285
Lys Glu Lys Ile Ala Ala Gln Leu Ser
                    290                 295

<210> SEQ ID NO 7
<211> LENGTH: 300
<212> TYPE: PRT
<213> ORGANISM: Bacillus anthracis

<400> SEQUENCE: 7

Met Val Lys Ile Thr Lys Asp Phe Ile Pro Val Gly His Ser Asn Arg
1               5                   10                  15
Pro Gly Tyr Thr Met Asp Pro Ala Tyr Ile Thr Val His Asn Thr Ala
                20                  25                  30
Asn Thr Ala Arg Gly Ala Ser Ala Ala Met His Ala Arg Tyr Glu Lys
            35                  40                  45
Asn Pro Glu Thr Pro Thr Ser Trp His Phe Thr Val Asp Asp Lys Glu
        50                  55                  60
Ile Tyr Gln His Leu Pro Leu Asn Glu Asn Gly Trp His Ala Gly Asp
65                  70                  75                  80
Gly Asn Arg Gly Thr Gly Asn Arg Lys Ser Ile Gly Ile Glu Ile Cys
                85                  90                  95
Glu Asn Ser Asp Gly Asp Phe Glu Lys Ala Val Ala Asn Ala Gln Trp
            100                 105                 110
Leu Ile Lys Lys Leu Met Lys Glu Gln Gly Ile Ser Leu Ala Asn Val
        115                 120                 125
Val Pro His Lys His Trp Ser Gly Lys Gln Cys Pro Arg Lys Leu Leu
    130                 135                 140
Asp Arg Trp Asp Ser Phe Lys Ala Gly Ile Ser Gly Ala Ser Ser Ser
145                 150                 155                 160
Ser Pro Glu Thr Lys Pro Gly Ala Thr Tyr Thr Val Lys Lys Gly Asp
                165                 170                 175
Thr Leu Ser Glu Ile Ala Val Lys Thr Gly Val Ser Met Ala Lys Leu
            180                 185                 190
Gln Ala Tyr Asn Gly Ile Lys Asn Ala Asn Lys Ile Thr Val Gly Gln
        195                 200                 205
Val Leu Lys Leu Thr Gly Ala Ala Gly Ser Ser Lys Pro Ser Ser Ser
    210                 215                 220
```

Gly Lys Lys Tyr Val Tyr Leu Pro Ala Ser Ala Asp Ser Trp Arg Ile
225                 230                 235                 240

Tyr Pro Thr Asn Lys Ala Pro Val Lys Gly Asn Glu Ile Asn Tyr Leu
            245                 250                 255

Arg Pro Lys Lys Phe Gly Gly Leu Lys Tyr Glu Ile Leu Ala Asn Pro
        260                 265                 270

Gln Thr Asp Val Tyr Thr Ile Lys Thr Asp Gln Phe Gly Lys Val Asn
    275                 280                 285

Ile Tyr Ala Ala Lys Ser Thr Gly Ala Thr Val Lys
290                 295                 300

<210> SEQ ID NO 8
<211> LENGTH: 272
<212> TYPE: PRT
<213> ORGANISM: Bacillus anthracis

<400> SEQUENCE: 8

Met Ala Ile Lys Val Val Lys Asn Leu Val Ser Lys Ser Lys Tyr Gly
1               5                   10                  15

Leu Lys Cys Pro Asn Pro Met Lys Ala Glu Tyr Ile Thr Ile His Asn
            20                  25                  30

Thr Ala Asn Asp Ala Ser Ala Asn Glu Ile Ser Tyr Met Lys Asn
        35                  40                  45

Asn Ser Ser Ser Thr Ser Phe His Phe Ala Val Asp Asp Lys Gln Val
    50                  55                  60

Ile Gln Gly Ile Pro Thr Asn Arg Asn Ala Trp His Thr Gly Asp Gly
65                  70                  75                  80

Thr Asn Gly Thr Gly Asn Arg Lys Ser Ile Gly Val Glu Ile Cys Tyr
                85                  90                  95

Ser Lys Ser Gly Gly Val Arg Tyr Lys Ala Ala Glu Lys Leu Ala Ile
            100                 105                 110

Lys Phe Val Ala Gln Leu Leu Lys Glu Arg Gly Trp Gly Ile Asp Arg
        115                 120                 125

Val Arg Lys His Gln Asp Trp Asn Gly Lys Tyr Cys Pro His Arg Ile
130                 135                 140

Leu Ser Glu Gly Arg Trp Ile Gln Val Lys Thr Ala Ile Glu Ala Glu
145                 150                 155                 160

Leu Lys Lys Leu Gly Gly Lys Thr Asn Ser Ser Lys Ala Ser Val Ala
                165                 170                 175

Lys Lys Lys Thr Thr Asn Thr Ser Ser Lys Thr Ser Tyr Ala Leu
            180                 185                 190

Pro Ser Gly Ile Phe Lys Val Lys Ser Pro Met Met Arg Gly Glu Lys
        195                 200                 205

Val Thr Gln Ile Gln Lys Ala Leu Ala Ala Leu Tyr Phe Tyr Pro Asp
210                 215                 220

Lys Gly Ala Lys Asn Asn Gly Ile Asp Gly Val Tyr Gly Pro Lys Thr
225                 230                 235                 240

Ala Asp Ala Ile Arg Arg Phe Gln Ser Met Tyr Cys Leu Thr Gln Asp
                245                 250                 255

Gly Ile Tyr Gly Pro Lys Thr Lys Ala Lys Leu Glu Ala Leu Leu Lys
            260                 265                 270